United States Patent [19]
Sonnewald

[11] Patent Number: 5,976,869
[45] Date of Patent: *Nov. 2, 1999

[54] DNA SEQUENCES AND PLASMIDS FOR THE PREPARATION OF PLANTS WITH CHANGED SUCROSE CONCENTRATION

[75] Inventor: Uwe Sonnewald, Berlin, Germany

[73] Assignee: Hoechst Schering AgrEvo GmbH, Berlin, Germany

[*] Notice: This patent is subject to a terminal disclaimer.

[21] Appl. No.: 08/778,656

[22] Filed: Jan. 3, 1997

Related U.S. Application Data

[62] Division of application No. 08/356,354, Dec. 20, 1994, Pat. No. 5,767,365, which is a continuation of application No. PCT/EP93/01605, Jun. 22, 1993.

[30] Foreign Application Priority Data

Jun. 24, 1992 [DE] Germany ............................. 42 20 758

[51] Int. Cl.[6] ............................. C12N 15/29; C12N 15/82
[52] U.S. Cl. ....................... 435/278; 435/320.1; 536/23.6
[58] Field of Search .................................. 536/23.2, 23.6; 435/320.1, 172.3, 419, 172.1, 468; 800/205, DIG. 42, 278, 298

[56] References Cited

PUBLICATIONS

Stam M, et al. "The silence of genes in transgenic plants." Ann. Bot. 79: 3–12, 1997.

Koziel MG, et al. "Optimizing expression of transgenes with an emphasis on post–transcriptional events." Plant Mol. Biol. 32: 393–405, 1996.

Smith CJS, et al. "Antisense RNA inhibition of polygalacturonase gene expression in transgenic tomatoes." Nature 334: 724–726, Aug. 25, 1988.

Worrell AC, et al. "Expression of a maize sucrose phosphate synthase in tomato alters leaf carbohydrate partitioning." Plant Cell 3: 1121–1130, 1991.

Salanoubat M, et al. Molecular cloning and sequencing of sucrose synthase cDNA from potato (*Solanum tuberosum* L.): Preliminary characterization of sucrose synthase mRNA distribution, 1987.

Carter P. "Site–directed mutagenesis." Biochem. J. 237: 1–7, 1986.

*Primary Examiner*—Lynette R. F. Smith
*Assistant Examiner*—Amy J. Nelson
*Attorney, Agent, or Firm*—Frommer Lawrence & Haug LLP

[57] ABSTRACT

This invention relates to DNA sequences and plasmids containing these sequences which can be integrated into a plant genome and which modify the activity of the sucrose-phosphate-synthase (sps) of the plant. The invention relates further to derivatives of the DNA sequences of the invention that are obtained by exchange of single bases or by deletion or insertion of base sequences and which code for proteins with comparable activity to sucrose-phosphate-synthase. Methods for transforming plant cells and regenerating plants from the cells which exhibit modified sucrose-phosphate-synthase activity are also described.

7 Claims, 3 Drawing Sheets

DNA SEQUENCES AND PLASMIDS FOR THE PREPARATION OF PLANTS WITH CHANGED SUCROSE CONCENTRATION

This is a division of application Ser. No. 08/356,354, filed Dec. 20, 1994, issued as U.S. Pat. No. 5,767,365, which is a 371 of PCT/EP93/01605, filed Jun. 22, 1993.

FIELD OF THE INVENTION

The present invention relates to DNA sequences and plasmids, containing these DNA sequences, which by integration into a plant genome, cause the activity of the sucrose-phosphate-synthase (SPS) of the plant to be changed and thus affect the sugar metabolism of the plant. The invention further relates to transgenic plants, in which through introduction of the DNA sequences, changes in the activity of the sucrose-phosphate-synthase are produced.

BACKGROUND OF THE INVENTION

Sucrose is of central importance for the plant and serves many functions. For the long distance transport of photoassimilates and/or energy between various organs in plants, sucrose is almost exclusively used. The sucrose, which is transported in a specific heterotrophic organ determines the growth and the development of this organ. Thus it is known, e.g. from EP 442 592, that transgenic plants, in which the transport of the sucrose away from the exporting leaves is inhibited by expression of an apoplastic invertase, shows a strong reduction in the growth of e.g. roots or tubers in the case of potato plants. For tobacco plants, the principal importance of sucrose for the long distance transport of energy carriers within the plant is described in von Schaewen et al, 1990, EMBO J 9: 3033–3044.

While it has been clearly shown that a reduction of the amount of sucrose imported in the heterotrophic organs, such as tubers and seeds, leads to loss of yield, it is not known whether an increase in the amount of sucrose in the photosynthetically active parts of the plant, mainly the leaves, leads to a better supply of heterotrophic organs and thus to an increase in yield.

A second central role for sucrose and/or the hexoses, glucose and fructose which are derived from sucrose, is in the protection of plants against frost damage at low temperatures. Frost damage is one of the main limiting factors in agricultural productivity in the northern hemisphere. Temperatures below freezing lead to the formation of ice crystals. Since the growing ice crystals consist of pure water, water is abstracted from the cells as the temperature falls.

This dehydration has at least two potential damaging results:

a) all dissolved substances within a cell are strongly concentrated and the cell contracts following the loss of water. Highly concentrated salts and organic acids lead to membrane damage;

b) with rehydration from dew, the previously contracted cells reexpand. The cell membrane also expands again. The volume expansion puts a heavy mechanical load on the membrane.

It is thus clear that a freezing/dew cycle can lead to severe membrane damage of the cells and thus to damage to the plant.

It thus appears worth while to hinder the freezing of plant cells. One possible strategy is to increase the formation of osmotically active substances in the cytosol of plant cells. This should lead to a lowering of the freezing point. Osmotically active substances include sucrose and/or the two hexoses which are derived from sucrose.

The increased formation of sucrose and/or the two hexoses at low temperatures is desirable in the growing plant. Another situation can exist in the harvested parts of a plant, especially in storage. For example, in potato tubers that are stored at 4–8° C., hexoses (glucose) accumulate. It would appear to be sensible, to see this as the answer to a lowering of the temperature ("cold-sweetening").

The accumulation of sucrose and glucose has in the case of potato tubers economically undesirable results. Increased amounts of reducing sugars, such as glucose, in potatoes which are fried when preparing crisps, chips and the like, leads to an undesirable browning due to the Maillard reaction. Such products with a dark brown colour are not generally acceptable to the consumer. Further the cooking strength is strongly dependent on the content of starch and/or its breakdown products which are important in determining the quality characteristics of the potato.

In relation to the economic aspects, sucrose thus possesses three especially important functions:

1 as the transport form for the distant transport of photoassimilates, 2 as an osmotically active substance with the desirable activity of lowering the freezing point in intact, growing plants, and 3 in the undesirable formation of reducing sugars in stored harvested parts of a plant, e.g. the potato tubers, as a result of low temperatures.

The biosynthesis pathways for the formation of sucrose, either from the primary photosynthesis products (in the leaf) or by breakdown of starch (in the storage organs e.g. of potatoes), are known. An enzyme in sucrose metabolism is sucrose-phosphate-synthase (SPS). It forms sucrose-6-phosphate from UDP-glucose and fructose-6-phosphate, which in a second step is converted to sucrose.

The isolation of SPS from maize and the cloning of a cDNA from mRNA from maize tissue is known (EP 466 995). In this application, processes for the purification of a protein such as by centrifuging of homogenates, differential precipitation and chromatography are described. A 300 times enrichment of SPS from plant tissue has been described by Salerno and Pontis (Planta 142: 41–48, 1978).

In view of the significance of SPS for carbohydrate metabolism it is questionable whether plants can tolerate a reduction in SPS activity in all or in certain organs. It is especially not known whether it is possible to produce transgenic plants with a reduced SPS activity. Also the use of SPS for the modification of the functions of sucrose for lowering the freezing point in intact plants and for the formation of reducing sugars in harvested parts is not known.

For the preparation of plants with reduced SPS activity, i.e. plants with changed sucrose concentration, it is necessary to make available an SPS coding region of such plant species, for which processes are described, whereby transgenic plants can be grown in large numbers. In as much as a reduction of SPS activity can be achieved, by selection from a large amount, the possibility exists of obtaining plants with such a phenotype. Further organ specific promoters for gene expression should exist for the plant species, by which the possibility of an organ specific reduction of the SPS activity could be investigated.

A species which fulfils the stated requirements is *Solanum tuberosum*. The genetic modification of *Solanum tuberosum* by gene transfer using Agrobacteria is well described (Fraley et al., 1985, Crit Rev Plant Sci 4: 1–46). Promoters for leaf specific (Stockhaus et al., 1989, Plant Cell 1: 805–813), tuber specific (EP 375 092) and wound inducing (EP 375 091) gene expression are known.

SUMMARY OF THE INVENTION

The present invention now provides DNA sequences with which changes of SPS activity are actually and demonstrably possible and with which the sucro se concentration in the plant can be modified. It is concerned which include sequences with the coding region of sucrose-phosphate-synthase (SPS) from *Solanum tuberosum*.

These DNA sequences can be introduced in plasmids and thereby combined with steering elements for expression in eukaryotic cells. Such steering elements are, on the one hand, transcription promoters and, on the other hand, transcription terminators.

Each plasmid comprises:

a) a suitable promoter that ensures that the coding sequence is read off at the suitable time point and/or in a specified development stage in the transgenic plants or in specified tissues of transgenic plants, b) at least one coding sequence, that
  i) is coupled to the promoter so that RNA can be translated into protein, whereby the protein demonstrates enzymatic activity that leads to a modification of the sucrose concentration in the plant, or
  ii) is coupled to the promoter so that the non-coding strand is read off, which leads to the formation of a so-called "anti-sense" RNA, which suppresses the formation of the coding protein of an endogenous gene in the plant which is involved in the sucrose biosynthesis, and c) a non-coding termination sequence that contains the signals for the termination and polyadenylation of the transcript.

The present invention further provides plasmids which include DNA sequences which change the SPS activity in the plant.

The coding sequences named under b) include the SPS sequences with the following nucleotide sequences:

```
SPS 1 sequence (seq. ID No. 1 No. 2):

CTATTCTCTC CCCTCCTTTT TCTCCTCTCT TCAACCCCAA AACTTCCCTT TCAAAGCCTT    60

TGCTTTCCCT TTCTCACTTA CCCAGATCAA CTAAGCCAAT TTGCTGTAGC CTCAGAAAAC   120

AGCATTCCCA GATTGAAAAA GAATCTTTTT CAGTACCCAA AAGTTGGGTT TCTCATGTCC   180

AGCAAGGATT AGCTGCTCTA GCTATTTCTT TAGCCCTTAA TTTTTGTCCA GTTGTGTCTT   240

CTGATTCTGC ATTGGCATCT GAATTTGATG TGTTAAATGA AGGGCCACCA AAGGACTCAT   300

ATGTAGTTGA TGATGCTGGT GTGCTTAGCA GGGTGACAAA GTCTGATTTG AAGGCATTGT   360

TGTCTGATGT GGAGAAGAGA AAAGGCTTCC ACATTAATTT CATCACTGTC CGCAAGCTCA   420

CTAGCAAAGC TGATGCTTTT GAGTATGCTG ACCAAGTTTT GGAGAAGTGG TACCCTAGTG   480

TTGAACAAGG AAATGATAAG GGTATAGTTG TGCTTGTTAC AAGTCAAAAG GAAGGCGCAA   540

TAACCGGTGG CCCTGATTTT GTAAAGGCCG TTGGAGATAC TGTTCTTGAT GCTACCGTCT   600

CAGAGAACCT TCCAGTGTTG GCTACTGAAG AGAAGTACAA TGAAGCAGTT TTCAGCACTG   660

CCACACGTCT TGTTGCAGCC ATTGATGGCC TTCCTGATCC TGGTGGACCC CAACTCAAGG   720

ATAACAAAAG AGAGTCCAAC TTCAAATCCA GAGAGGAAAC TGATGAGAAA AGAGGACAAT   780

TCACACTTGT GGTTGGTGGG CTGTTAGTGA TTGCTTTTGT TGTTCCTATG GCTCAATACT   840

ATGCATATGT TTCAAAGAAG TGAACTGTCT GATTCTGGAA AGTTACATTT TCGTGAGATT   900

TGAGTAAGCA TGTATATTAT CGTGTACAAA ATGGTCCATT CGGAAATGAC TGATTC       956

ATG AGA TAT TTA AAA AGG ATA AAT ATG AAG ATT TGG ACC TCC CCT        1001
Met Arg Tyr Leu Lys Arg Ile Asn Met Lys Ile Trp Thr Ser Pro
1             5                   10                  15

AAC ATA ACG GAT ACT GCC ATT TCT TTT TCA GAG ATG CTG ACG CCA        1046
Asn Ile Thr Asp Thr Ala Ile Ser Phe Ser Glu Met Leu Thr Pro
              20                  25                  30

ATA AGT ACA GAC GGC TTG ATG ACT GAG ATG GGG GAG AGT AGT GGT        1091
Ile Ser Thr Asp Gly Leu Met Thr Glu Met Gly Glu Ser Ser Gly
              35                  40                  45

GCT TAT ATT ATT CGC ATT CCT TTT GGA CCA AGA GAG AAA TAT ATT        1136
Ala Tyr Ile Ile Arg Ile Pro Phe Gly Pro Arg Glu Lys Tyr Ile
              50                  55                  60

CCA AAA GAA CAG CTA TGG CCC TAT ATT CCC GAA TTT GTT GAT GGT        1181
```

-continued

```
                Pro Lys Glu Gln Leu Trp Pro Tyr Ile Pro Glu Phe Val Asp Gly
                                 65                  70                  75

GCA CTT AAC CAT ATT ATT CAA ATG TCC AAA GTT CTT GGG GAG CAA              1226
Ala Leu Asn His Ile Ile Gln Met Ser Lys Val Leu Gly Glu Gln
                 80                  85                  90

ATT GGT AGT GGC TAT CCT GTG TGG CCT GTT GCC ATA CAC GGA CAT              1271
Ile Gly Ser Gly Tyr Pro Val Trp Pro Val Ala Ile His Gly His
                 95                 100                 105

TAT GCT GAT GCT GGC GAC TCA GCT GCT CTC CTG TCA GGT GCT TTA              1316
Tyr Ala Asp Ala Gly Asp Ser Ala Ala Leu Leu Ser Gly Ala Leu
                110                 115                 120

AAT GTA CCA ATG CTT TTC ACT GGT CAC TCA CTT GGT AGA GAT AAG              1361
Asn Val Pro Met Leu Phe Thr Gly His Ser Leu Gly Arg Asp Lys
                125                 130                 135

TTG GAG CAA CTG TTG CGA CAA GGT CGT TTG TCA AAG GAT GAA ATA              1406
Leu Glu Gln Leu Leu Arg Gln Gly Arg Leu Ser Lys Asp Glu Ile
                140                 145                 150

AAC TCA ACC TAC AAG ATA ATG CGG AGA ATA GAG GCT GAA GAA TTA              1451
Asn Ser Thr Tyr Lys Ile Met Arg Arg Ile Glu Ala Glu Glu Leu
                155                 160                 165

ACT CTT GAT GCT TCC GAA ATT GTC ATC ACT AGT ACA AGA CAG GAG              1496
Thr Leu Asp Ala Ser Glu Ile Val Ile Thr Ser Thr Arg Gln Glu
                170                 175                 180

ATT GAC GAG CAA TGG CGT TTG TAT GAT GGG TTT GAT CCA ATA TTA              1541
Ile Asp Glu Gln Trp Arg Leu Tyr Asp Gly Phe Asp Pro Ile Leu
                185                 190                 195

GAG CGT AAG TTA CGT GCA AGG ATC AAG CGC AAT GTC AGC TGT TAT              1586
Glu Arg Lys Leu Arg Ala Arg Ile Lys Arg Asn Val Ser Cys Tyr
                200                 205                 210

GGC AGG TTT ATG CCT CGT ATG GCT GTA ATT CCT CCT GGG ATG GAG              1631
Gly Arg Phe Met Pro Arg Met Ala Val Ile Pro Pro Gly Met Glu
                215                 220                 225

TTC CAC CAT ATT GTG CCA CAT GAA GGT GAC ATG GAT GGA GAA ACA              1676
Phe His His Ile Val Pro His Glu Gly Asp Met Asp Gly Glu Thr
                230                 235                 240

GAA GGA AGT GAA GAT GGG AAG ACC CCG GAT CCA CCT ATT TGG GCA              1721
Glu Gly Ser Glu Asp Gly Lys Thr Pro Asp Pro Pro Ile Trp Ala
                245                 250                 255

GAG ATT ATG CGC TTC TTT TCT AAT CCA AGG AAG CCT ATG ATA CTC              1766
Glu Ile Met Arg Phe Phe Ser Asn Pro Arg Lys Pro Met Ile Leu
                260                 265                 270

GCA CTT GCT AGG CCT GAT CCC AAG AAG AAC CTC ACT ACT TTA GTG              1811
Ala Leu Ala Arg Pro Asp Pro Lys Lys Asn Leu Thr Thr Leu Val
                275                 280                 285

AAA GCA TTT GGT GAA TGT CGT CCA TTG AGA GAG CTT GCT AAT CTT              1856
Lys Ala Phe Gly Glu Cys Arg Pro Leu Arg Glu Leu Ala Asn Leu
                290                 295                 300

ACT TTG ATA ATG GGT AAT CGA GAT AAT ATC GAC GAA ATG TCT AGC              1901
Thr Leu Ile Met Gly Asn Arg Asp Asn Ile Asp Glu Met Ser Ser
                305                 310                 315

ACC AAT TCT GCA CTT CTT CTT TCA ATC TTG AAA ATG ATA GAT AAG              1946
Thr Asn Ser Ala Leu Leu Leu Ser Ile Leu Lys Met Ile Asp Lys
                320                 325                 330

TAT GAT CTT TAT GGT CAA GTA GCT TAT CCT AAA CAC CAC AAG CAG              1991
Tyr Asp Leu Tyr Gly Gln Val Ala Tyr Pro Lys His His Lys Gln
                335                 340                 345

TCA GAT GTT CCT GAT ATC TAC CGT CTT GCT GCA AAG ACT AAG GGT              2036
Ser Asp Val Pro Asp Ile Tyr Arg Leu Ala Ala Lys Thr Lys Gly
                350                 355                 360

GTT TTT ATT AAT CCA GCT TTT ATT GAG CCT TTT GGA CTG ACT TTG              2081
```

-continued

```
Val Phe Ile Asn Pro Ala Phe Ile Glu Pro Phe Gly Leu Thr Leu
            365                 370                 375

ATT GAG GCA GCA GCT TAT GGT CTC CCA ATG GTA GCC ACA AAA AAT      2126
Ile Glu Ala Ala Ala Tyr Gly Leu Pro Met Val Ala Thr Lys Asn
            380                 385                 390

GGA GGA CCT GTT GAT ATA CAT AGG GTT CTT GAC AAT GGT CTC TTA      2171
Gly Gly Pro Val Asp Ile His Arg Val Leu Asp Asn Gly Leu Leu
            395                 400                 405

GTG GAT CCC CAT GAT CAG CAG GCA ATT GCT GAT GCT CTT TTG AAG      2216
Val Asp Pro His Asp Gln Gln Ala Ile Ala Asp Ala Leu Leu Lys
            410                 415                 420

TTG GTT GCT GAT AAG CAA CTG TGG GCT AAA TGC AGG GCA AAT GGA      2261
Leu Val Ala Asp Lys Gln Leu Trp Ala Lys Cys Arg Ala Asn Gly
            425                 430                 435

TTA AAA AAT ATC CAC CTT TTC TCA TGG CCC GAG CAC TGT AAA ACT      2306
Leu Lys Asn Ile His Leu Phe Ser Trp Pro Glu His Cys Lys Thr
            440                 445                 450

TAT CTA TCC CCG ATA GCT AGC TGC AAA CCA AGG CAA CCA CGC TCG      2351
Tyr Leu Ser Arg Ile Ala Ser Cys Lys Pro Arg Gln Pro Arg Trp
            455                 460                 465

CTG AGA TCC ATT GAT GAT GAT GAT GAA AAT TCA GAA ACA GAT TCA      2296
Leu Arg Ser Ile Asp Asp Asp Asp Glu Asn Ser Glu Thr Asp Ser
            470                 475                 480

CCT AGT GAT TCC TTG AGA GAT ATT CAT GAT ATA TCT CTG AAT TTG      2441
Pro Ser Asp Ser Leu Arg Asp Ile His Asp Ile Ser Leu Asn Leu
            485                 490                 495

AGA TTT TCA TTA GAT GGG GAA AAG AAT GAC AAT AAA GAA AAT GCT      2486
Arg Phe Ser Leu Asp Gly Glu Lys Asn Asp Asn Lys Glu Asn Ala
            500                 505                 510

GAT AAT ACA TTA GAC CCC GAA GTT CGA AGG AGC AAG TTA GAG AAT      2531
Asp Asn Thr Leu Asp Pro Glu Val Arg Arg Ser Lys Leu Glu Asn
            515                 520                 525

GCT GTT TTG TCC TTA TCT AAG GGT GCA CTG AAG AGC ACA TCA AAA      2576
Ala Val Leu Ser Leu Ser Lys Gly Ala Leu Lys Ser Thr Ser Lys
            530                 535                 540

TCT TGG TCG TCA GAC AAG GCA GAC CAA AAC CCT GGT GCT GGT AAA      2621
Ser Trp Ser Ser Asp Lys Ala Asp Gln Asn Pro Gly Ala Gly Lys
            545                 550                 555

TTC CCA GCG ATT AGG AGG AGG CGA CAT ATT TTT GTT ATT GCA GTG      2666
Phe Pro Ala Ile Arg Arg Arg Arg His Ile Phe Val Ile Ala Val
            560                 560                 565

GAT TGT GAT GCT AGC TCA GGA CTC TCT GGA AGT GTG AAA AAG ATA      2711
Asp Cys Asp Ala Ser Ser Gly Leu Ser Gly Ser Val Lys Lys Ile
            570                 575                 580

TTT GAG GCT GTA GAG AAG GAA AGG GCA GAG GGT TCC ATT GGA TTT      2756
Phe Glu Ala Val Glu Lys Glu Arg Ala Glu Gly Ser Ile Gly Phe
            585                 590                 595

ATC CTG GCT ACA TCT TTC AAT ATA TCA GAA GTA CAG TCT TTC CTG      2801
Ile Leu Ala Thr Ser Phe Asn Ile Ser Glu Val Gln Ser Phe Leu
            600                 605                 610

CTT TCA GAG GGC ATG AAT CCT ACT GAT TTT GAT GCT TAC ATA TGC      2846
Leu Ser Glu Gly Met Asn Pro Thr Asp Phe Asp Ala Tyr Ile Cys
            615                 620                 625

AAT AGT GGT GGT GAT CTT TAT TAT TCG TCC TTC CAT TCT GAG CAA      2891
Asn Ser Gly Gly Asp Leu Tyr Tyr Ser Ser Phe His Ser Glu Gln
            630                 635                 640

AAT CCT TTT GTA GTT GAC TTG TAC TAT CAC TCA CAT ATT GAG TAT      2936
Asn Pro Phe Val Val Asp Leu Tyr Tyr His Ser His Ile Glu Tyr
            645                 650                 655

CGT TGG GGG GGC GAA GGA TTG AGA AAG ACT TTG GTG CGT TGG GCC      2981
```

-continued

```
Arg Trp Gly Gly Glu Gly Leu Arg Lys Thr Leu Val Arg Trp Ala
            660             665             670

GCC TCT ATC ATT GAT AAG AAT GGT GAA AAT GGA GAT CAC ATT GTT        3026
Ala Ser Ile Ile Asp Lys Asn Gly Glu Asn Gly Asp His Ile Val
            675             680             685

GTT GAG GAT GAA GAC AAT TCA GCT GAC TAC TGC TAT ACT TTC AAA        3071
Val Glu Asp Glu Asp Asn Ser Ala Asp Tyr Cys Tyr Thr Phe Lys
            690             695             700

GTC TGC AAG CCT GGG ACG GTT CCT CCA TCT AAA GAG CTT AGA AAA        3116
Val Cys Lys Pro Gly Thr Val Pro Pro Ser Lys Glu Leu Arg Lys
            705             710             715

GTA ATG CGA ATT CAG GCA CTT CGT TGT CAC GCT GTT TAT TGT CAA        3161
Val Met Arg Ile Gln Ala Leu Arg Cys His Ala Val Tyr Cys Gln
            720             725             730

AAT GGG AGT AGG ATT AAT GTG ATC CCT GTA CTG GCA TCT CGG TCC        3206
Asn Gly Ser Arg Ile Asn Val Ile Pro Val Leu Ala Ser Arg Ser
            735             740             745

CAA GCA CTC AGG TAC TTA TAT CTG CGA TGG GGA ATG GAC TTG TCG        3251
Gln Ala Leu Arg Tyr Leu Tyr Leu Arg Trp Gly Met Asp Leu Ser
            750             755             760

AAG TTG GTG GTT TTC GTC GGA GAA AGT GGT GAT ACC GAT TAT GAA        3296
Lys Leu Val Val Phe Val Gly Glu Ser Gly Asp Thr Asp Tyr Glu
            765             770             775

GGA TTA ATC GGT GGT CTA CGC AAG GCT GTC ATA ATG AAA GGC CTC        3341
Gly Leu Ile Gly Gly Leu Arg Lys Ala Val Ile Met Lys Gly Leu
            780             785             790

TGC ACT AAT GCA AGC AGC TTA ATT CAC GGT AAT AGG AAT TAC CCG        3386
Cys Thr Asn Ala Ser Ser Leu Ile His Gly Asn Arg Asn Tyr Pro
            795             800             805

CTA TCT GAT GTT TTA CCA TTC GAC AGC CCT AAT GTC ATC CAA GCG        3431
Leu Ser Asp Val Leu Pro Phe Asp Ser Pro Asn Val Ile Gln Ala
            810             815             820

GAC GAG GAA TGT AGC AGC ACC GAA ATC CGT TGC TTA CTG GTG AAA        3476
Asp Glu Glu Cys Ser Ser Thr Glu Ile Arg Cys Leu Leu Val Lys
            825             830             835

CTA GCG GTA CTC AAA GGA TAATACCCTT CCCCCTTTGA TTGTCAAAAA           3524
Leu Ala Val Leu Lys Gly
            840

CCTATATGAG CTATAAGACT ATGCCATGAA AAGAATGGCC ATCCATTTGG CTTGTCTTTT  3584

GAAGCTGTTA ATACTTTTCA ACAGACTACA AAATGAGATG AGTCCTTTGA TCCTCTTTAA  3644

AGGACATAAA AGCTTTATGC AAGAACCAGT GCTGTAAAGT TATAGAATTT CTTTTGCTAT  3704

ATATGACATT CGACAGAACC TGTTCCGGTT CATCGA                            3740
```

SPS 2 sequence (Seq. ID No. 3 and No. 4)

```
ATTTTTTTCT CTAAGTTCTC TCTCGCTGTC CTTATCATTT CACCACCTCC ATAAATCTAG    60

AAACATCTTT TCTACTCCGT TAATCTCTCT AGCACACGGC GGAGGAGTGC GGCGGAGGAG   120

ATG GCG GGA AAC GAT TGG ATT AAC AGT TAC TTA GAG GCG ATA CTG          165
Met Ala Gly Asn Asp Trp Ile Asn Ser Tyr Leu Glu Ala Ile Leu
1           5               10              15

GAT GTT GGA CCA GGG CTA GAT GAT AAG AAG TCA TCG TTG TTG TTG          210
Asp Val Gly Pro Gly Leu Asp Asp Lys Lys Ser Ser Leu Leu Leu
            20              25              30

AGA GAA AGA GGG AGG TTT AGT CCG ACG AGG TAC TTT GTT GAG GAA          255
Arg Glu Arg Gly Arg Phe Ser Pro Thr Arg Tyr Phe Val Glu Glu
            35              40              45

GTT ATT ACT GGA TTC GAT GAG ACT GAT TTG CAT CGT TCG TGG ATC          300
Val Ile Thr Gly Phe Asp Glu Thr Asp Leu His Arg Ser Trp Ile
            50              55              60
```

-continued

```
CGA GCA CAA GCT ACT CGG AGT CCG CAG AGA AGG AAT ACT AGG CTC      345
Arg Ala Gln Ala Thr Arg Ser Pro Gln Arg Arg Asn Thr Arg Leu
             65                  70                  75

GAG AAT ATG TGC TGG AGG ATT TGG AAT TTG GCT CGC CAG AAA AAG      390
Glu Asn Met Cys Trp Arg Ile Trp Asn Leu Ala Arg Gln Lys Lys
             80                  85                  90

CAG CTT GAG GGA GAG CAA GCT CAG TGG ATG GCA AAA CGC CGT CAA      435
Gln Leu Glu Gly Glu Gln Ala Gln Trp Met Ala Lys Arg Arg Gln
             95                 100                 105

GAA CGT GAA AGA GGT CGC AGA GAA GCA GTT GCT GAT ATG TCA GAG      480
Glu Arg Glu Arg Gly Arg Arg Glu Ala Val Ala Asp Met Ser Glu
            110                 115                 120

GAT CTA TCT GAG GGA GAG AAA GGA GAT ATA GTC GCT GAC ATG TCA      525
Asp Leu Ser Glu Gly Glu Lys Gly Asp Ile Val Ala Asp Met Ser
            125                 130                 135

TCT CAT GGT GAA AGT ACC AGA GGC CGA TTG CCT AGA ATC AGT TCT      570
Ser His Gly Glu Ser Thr Arg Gly Arg Leu Pro Arg Ile Ser Ser
            140                 145                 150

GTT GAG ACA ATG GAA GCA TGG GTC AGT CAG CAG AGA GGA AAG AAG      615
Val Glu Thr Met Glu Ala Trp Val Ser Gln Gln Arg Gly Lys Lys
            155                 160                 165

CTT TAT ATC GTG CTT ATA AGT TTA CAT GGT TTA ATT CGG GGT GAG      660
Leu Tyr Ile Val Leu Ile Ser Leu His Gly Leu Ile Arg Gly Glu
            170                 175                 180

AAT ATG GAG CTT GGA CGG GAT TCT GAT ACT GGT GGT CAG GTG AAG      705
Asn Met Glu Leu Gly Arg Asp Ser Asp Thr Gly Gly Gln Val Lys
            185                 190                 195

TAT GTT GTT GAA CTT GCG AGG GCC TTA GGG TCG ATG CCA GGT GTA      750
Tyr Val Val Glu Leu Ala Arg Ala Leu Gly Ser Met Pro Gly Val
            200                 205                 210

TAT CGG GTT GAC TTG CTT ACT AGA CAA GTA TCT TCA CCA GAA GTA      795
Tyr Arg Val Asp Leu Leu Thr Arg Gln Val Ser Ser Pro Glu Val
            215                 220                 225

GAT TGG AGC TAT GGT GAG CCG ACA GAG ATG CTG ACG CCA ATA AGT      840
Asp Trp Ser Tyr Gly Glu Pro Thr Glu Met Leu Thr Pro Ile Ser
            230                 235                 240

ACA GAC GGC TTG ATG ACT GAG ATG GGG GAG AGT AGT GGT GCT TAT      885
Thr Asp Gly Leu Met Thr Glu Met Gly Glu Ser Ser Gly Ala Tyr
            245                 250                 255

ATT ATT CGC ATT CCT TTT GGA CCA AGA GAG AAA TAT ATT CCA AAA      930
Ile Ile Arg Ile Pro Phe Gly Pro Arg Glu Lys Tyr Ile Pro Lys
            260                 265                 270

GAA CAG CTA TGG CCC TAT ATT CCC GAA TTT GTT GAT GGT GCA CTT      975
Glu Gln Leu Trp Pro Tyr Ile Pro Glu Phe Val Asp Gly Ala Leu
            275                 280                 285

AAC CAT ATT ATT CAA ATG TCC AAA GTT CTT GGG GAG CAA ATT GGT     1020
Asn His Ile Ile Gln Met Ser Lys Val Leu Gly Glu Gln Ile Gly
            290                 295                 300

AGT GGC TAT CCT GTG TGG CCT GTT GCC ATA CAC GGA CAT TAT GCT     1065
Ser Gly Tyr Pro Val Trp Pro Val Ala Ile His Gly His Tyr Ala
            305                 310                 315

GAT GCT GGC GAC TCA GCT GCT CTC CTG TCA GGT GCT TTA AAT GTA     1110
Asp Ala Gly Asp Ser Ala Ala Leu Leu Ser Gly Ala Leu Asn Val
            320                 330                 335

CCA ATG CTT TTC ACT GGT CAC TCA CTT GGT AGA GAT AAG TTG GAG     1155
Pro Met Leu Phe Thr Gly HIs Ser Leu Gly Arg Asp Lys Leu Glu
            340                 345                 350

CAA CTG TTG GCA CAA GGT CGA AAG TCA AAG GAT GAA ATA AAC TCA     1200
Gln Leu Leu Ala Gln Gly Arg Lys Ser Lys Asp Glu Ile Asn Ser
            355                 360                 365
```

-continued

```
ACC TAC AAG ATA ATG CGG AGA ATA GAG GCT GAA GAA TTA ACT CTT      1245
Thr Tyr Lys Ile Met Arg Arg Ile Glu Ala Glu Glu Leu Thr Leu
                370                 375                 380

GAT GCT TCC GAA ATT GTC ATC ACT AGT ACA AGA CAG GAG ATT GAC      1290
Asp Ala Ser Glu Ile Val Ile Thr Ser Thr Arg Gln Glu Ile Asp
                385                 390                 395

GAG CAA TGG CGT TTG TAT GAT GGG TTT GAT CCA ATA TTA GAG CGT      1335
Glu Gln Trp Arg Leu Tyr Asp Gly Phe Asp Pro Ile Leu Glu Arg
                400                 405                 410

AAG TTA CGT GCA AGG ATC AAG CGC AAT GTC AGC TGT TAT GGC AGG      1380
Lys Leu Arg Ala Arg Ile Lys Arg Asn Val Ser Cys Tyr Gly Arg
                415                 420                 425

TTT ATG CCT CGT ATG GCT GTA ATT CCT CCT GGG ATG GAG TTC CAC      1425
Phe Met Pro Arg Met Ala Val Ile Pro Pro Gly Met Glu Phe His
                430                 435                 440

CAT ATT GTG CCA CAT GAA GGT GAC ATG GAT GGT GAA ACA GAA GGA      1470
His Ile Val Pro His Glu Gly Asp Met Asp Gly Glu Thr Glu Gly
                445                 450                 455

AGT GAA GAT GGG AAG ACC CCG GAT CCA CCT ATT TGG GCA GAG ATT      1515
Ser Glu Asp Gly Lys Thr Pro Asp Pro Pro Ile Trp Ala Glu Ile
                460                 465                 470

ATG CGC TTC TTT TCT AAT CCA AGG AAG CCT ATG ATA CTC GCA CTT      1560
Met Arg Phe Phe Ser Asn Pro Arg Lys Pro Met Ile Leu Ala Leu
                475                 480                 485

GCT AGG CCT GAT CCC AAG AAG AAC CTC ACT ACT TTA GTG AAA GCA      1605
Ala Arg Pro Asp Pro Lys Lys Asn Leu Thr Thr Leu Val Lys Ala
                490                 495                 500

TTT GGT GAA TGT CGT CCA TTG AGA GAG CTT GCT AAT CTT ACT TTG      1650
Phe Gly Glu Cys Arg Pro Leu Arg Glu Leu Ala Asn Leu Thr Leu
                505                 510                 515

ATA ATG GGT AAT CGA GAT AAT ATC GAC GAA ATG TCT AGC ACC AAT      1695
Ile Met Gly Asn Arg Asp Asn Ile Asp Glu Met Ser Ser Thr Asn
                520                 525                 530

TCT GCA CTT CTT CTT TCA ATC TTG AAA ATG ATA GAT AAG TAT GAT      1740
Ser Ala Leu Leu Leu Ser Ile Leu Lys Met Ile Asp Lys Tyr Asp
                535                 540                 540

CTT TAT GGT CAA GTA GCT TAT CCT AAA CAC CAC AAG CAG TCA GAT      1785
Leu Tyr Gly Gln Val Ala Tyr Pro Lys His His Lys Gln Ser Asp
                545                 550                 555

GTT CCT GAT ATC TAC CGT CTT GCT GCA AAG ACT AAG GGT GTT TTT      1830
Val Pro Asp Ile Tyr Arg Leu Ala Ala Lys Thr Lys Gly Val Phe
                560                 565                 570

ATT AAT CCA GCT TTT ATT GAG CCT TTT GGA CTG ACT TTG ATT GAG      1875
Ile Asn Pro Ala Phe Ile Glu Pro Phe Gly Leu Thr Leu Ile Glu
                575                 580                 585

GCA GCA GCT TAT GGT CTC CCA ATG GTA GCC ACA AAA AAT GGA GGA      1920
Ala Ala Ala Tyr Gly Leu Pro Met Val Ala Thr Lys Asn Gly Gly
                590                 595                 600

CCT GTT GAT ATA CAT AGG GTT CTT GAC AAT GGT CTC TTA GTG GAT      1965
Pro Val Asp Ile His Arg Val Leu Asp Asn Gly Leu Leu Val Asp
                605                 610                 615

CCC CAT GAT CAG CAG GCA ATT GCT GAT GCT CTT TTG AAG TTG GTT      2010
Pro His Asp Gln Gln Ala Ile Ala Asp Ala Leu Leu Lys Leu Val
                620                 625                 620

GCT GAT AAG CAA CTG TGG GCT AAA TGC AGG GCA AAT GGA TTA AAA      2055
Ala Asp Lys Gln Leu Trp Ala Lys Cys Arg Ala Asn Gly Leu Lys
                635                 640                 645

AAT ATC CAC CTT TTC TCA TGG CCC GAG CAC TGT AAA ACT TAT CTA      2100
Asn Ile His Leu Phe Ser Trp Pro Glu His Cys Lys Thr Tyr Leu
                650                 655                 660
```

```
TCC CGG ATA GCT AGC TGC AAA CCA AGG CAA CCA CGC TGG CTG AGA      2145
Ser Arg Ile Ala Ser Cys Lys Pro Arg Gln Pro Arg Trp Leu Arg
                665                 670                 675

TCC ATT GAT GAT GAT GAT GAA AAT TCA GAA ACA GAT TCA CCT AGT      2190
Ser Ile Asp Asp Asp Asp Glu Asn Ser Glu Thr Asp Ser Pro Ser
                680                 685                 690

GAT TCC TTG AGA GAT ATT CAT GAT ATA TCT CTG AAT TTG AGA TTT      2235
Asp Ser Leu Arg Asp Ile His Asp Ile Ser Leu Asn Leu Arg Phe
                695                 700                 705

TCA TTA GAT GGG GAA AAG AAT GAC AAT AAA GAA AAT GCT GAT AAT      2280
Ser Leu Asp Gly Glu Lys Asn Asp Asn Lys Glu Asn Ala Asp Asn
                710                 715                 720

ACA TTA GAC CCC GAA GTT CGA AGG AGC AAG TTA GAG AAT GCT GTT      2325
Thr Leu Asp Pro Glu Val Arg Arg Ser Lys Leu Glu Asn Ala Val
                725                 730                 735

TTG TCC TTA TCT AAG GGT GCA CTG AAG AGC ACA TCA AAA TCT TGG      2370
Leu Ser Leu Ser Lys Gly Ala Leu Lys Ser Thr Ser Lys Ser Trp
                740                 745                 750

TCG TCA GAC AAG GCA GAC CAA AAC CCT GGT GCT GGT AAA TTC CCA      2415
Ser Ser Asp Lys Ala Asp Gln Asn Pro Gly Ala Gly Lys Phe Pro
                755                 760                 765

GCG ATT AGG AGG AGG CGA CAT ATT TTT GTT ATT GCA GTG GAT TGT      2460
Ala Ile Arg Arg Arg Arg His Ile Phe Val Ile Ala Val Asp Cys
                770                 775                 780

GAT GCT AGC TCA GGA CTC TCT GGA AGT GTG AAA AAG ATA TTT GAG      2505
Asp Ala Ser Ser Gly Leu Ser Gly Ser Val Lys Lys Ile Phe Glu
                785                 790                 795

GCT GTA GAG AAG GAA AGG GCA GAG GGT TCC ATT GGA TTT ATC CTG      2550
Ala Val Glu Lys Glu Arg Ala Glu Gly Ser Ile Gly Phe Ile Leu
                800                 805                 810

GCT ACA TCT TTC AAT ATA TCA GAA GTA CAG TCT TTC CTG CTT TCA      2595
Ala Thr Ser Phe Asn Ile Ser Glu Val Gln Ser Phe Leu Leu Ser
                815                 820                 825

GAG GGC ATG AAT CCT ACT GAT TTT GAT GCT TAC ATA TGC AAT AGT      2640
Glu Gly Met Asn Pro Thr Asp Phe Asp Ala Tyr Ile Cys Asn Ser
                830                 835                 840

GGT GGT GAT CTT TAT TAT TCG TCC TTC CAT TCT GAG CAA AAT CCT      2685
Gly Gly Asp Leu Tyr Tyr Ser Ser Phe His Ser Glu Gln Asn Pro
                845                 850                 855

TTT GTA GTT GAC TTG TAC TAT CAC TCA CAT ATT GAG TAT CGT TGG      2730
Phe Val Val Asp Leu Tyr Tyr His Ser His Ile Glu Tyr Arg Trp
                860                 865                 870

GGG GGC GAA GGA TTG AGA AAG ACT TTG GTG CGT TGG GCC GCC TCT      2775
Gly Gly Glu Gly Leu Arg Lys Thr Leu Val Arg Trp Ala Ala Ser
                875                 880                 885

ATC ATT GAT AAG AAT GGT GAA AAT CGA GAT CAC ATT GTT GTT GAG      2820
Ile Ile Asp Lys Asn Gly Glu Asn Arg Asp His Ile Val Val Glu
                890                 895                 900

GAT GAA GAC AAT TCA GCT GAC TAC TGC TAT ACT TTC AAA GTC TGC      2865
Asp Glu Asp Asn Ser Ala Asp Tyr Cys Tyr Thr Phe Lys Val Cys
                905                 910                 915

AAG CCT GGG ACG GTT CCT CCA TCT AAA GAG CTT AGA AAA GTA ATG      2910
Lys Pro Gly Thr Val Pro Pro Ser Lys Glu Leu Arg Lys Val Met
                920                 925                 930

CGA ATT CAG GCA CTT CGT TGT CAC GCT GTT TAT TGT CAA AAT GGG      2955
Arg Ile Gln Ala Leu Arg Cys His Ala Val Tyr Cys Gln Asn Gly
                935                 940                 945

AGT AGG ATT AAT GTG ATC CCT GTA CTG GCA TCT CGG TCC CAA GCA      3000
Ser Arg Ile Asn Val Ile Pro Val Leu Ala Ser Arg Ser Gln Ala
                950                 955                 960
```

```
CTC AGG TAC TTA TAT CTG CGA TGG GGA ATG GAC TTG TCG AAG TTG       3045
Leu Arg Tyr Leu Tyr Leu Arg Trp Gly Met Asp Leu Ser Lys Leu
            965                 970                 975

GTG GTT TTC GTC GGA GAA AGT GGT GAT ACC GAT TAT GAA GGA TTA       3090
Val Val Phe Val Gly Glu Ser Gly Asp Thr Asp Tyr Glu Gly Leu
            980                 985                 990

ATC GGT GGT CTA CGC AAG GCT GTC ATA ATG AAA GGC CTC TGC ACT       3135
Ile Gly Gly Leu Arg Lys Ala Val Ile Met Lys Gly Leu Cys Thr
            995                 1000                1005

AAT GCA AGC AGC TTA ATT CAC GGT AAT AGG AAT TAC CCG CTA TCT       3180
Asn Ala Ser Ser Leu Ile His Gly Asn Arg Asn Tyr Pro Leu Ser
            1010                1015                1020

GAT GTT TTA CCA TTC GAC AGC CCT AAT GTC ATC CAA GCG GAC GAG       3225
Asp Val Leu Pro Phe Asp Ser Pro Asn Val Ile Gln Ala Asp Glu
            1025                1030                1035

GAA TGT AGC AGC ACC GAA ATC CGT TGC TTA CTG GAG AAA CTA GCG       3270
Glu Cys Ser Ser Thr Glu Ile Arg Cys Leu Leu Glu Lys Leu Ala
            1040                1045                1050

GTA CTC AAA GGA TAA TACCCTTCCC CCTTTGATTG TCAAAAACCT              3315
Val Leu Lys Gly End
            1054

ATATGAGCTA TAAGACTATG CCATGAAAAG AATGGCCATC CATTTGGCTT GTCTTTTGAA 3375

GCTGTTAATA CTTTTCAACA GACTACAAAA TGAGATGAGT CCTTTGATCC TCTTTAAAGG 3435

ACATAAAAGC TTTATGCAAG AACCAGTGCT GTAAAGTTAT AGAATTTCTT TTGCTATATA 3495

TGACATTCGA CAGAACCAGT TCCGGTTCAT CGAGAAAAAG AAATAAATTT CAACTTATAA 3555

ACATGCCTGA TCATGTAAAT TATCATATAC ATCCATCGGA AGGCATTATC GATGGGTTAT 3615

CAGATTTTTT                                                        3625

SPS 3 sequence (Seq. ID No. 5 and No. 6)

ATTTTTT TCTCTAAATT CTCTCTCACT GTCCTTATCA TTTCACCACC TCCATAAATC  57

TAGAAACATC TTTTCTATTC CGTTAATCTC TCTAGCACAC GGCGGAGTGC GGCGGAGGAG  117

ATG GCG GGA AAC GAC TGG ATT AAC AGT TAC TTA GAG GCG ATA CTG       162
Met Ala Gly Asn Asp Trp Ile Asn Ser Tyr Leu Glu Ala Ile Leu
1           5                   10                  15

GAT GTA GGA CCA GGG CTA GAT GAT AAG AAA TCA TCG TTG TTG TTG       207
Asp Val Gly Pro Gly Leu Asp Asp Lys Lys Ser Ser Leu Leu Leu
            20                  25                  30

AGA GAA AGA GGG AGG TTT AGT CCG ACG AGG TAC TTT GTT GAG GAA       252
Arg Glu Arg Gly Arg Phe Ser Pro Thr Arg Tyr Phe Val Glu Glu
            35                  40                  45

GTT ATT ACT GGA TTC GAT GAG ACT GAT TTG CAT CGC TCG TGG ATC       297
Val Ile Thr Gly Phe Asp Glu Thr Asp Leu His Arg Ser Trp Ile
            50                  55                  60

CGA GCA CAA GCT ACT CGG AGT CCG CAG GAG AGG AAT ACT AGG CTC       342
Arg Ala Gln Ala Thr Arg Ser Pro Gln Glu Arg Asn Thr Arg Leu
            65                  70                  75

GAG AAT ATG TGC TGG AGG ATT TGG AAT TTG GCT CGC CAG AAA AAG       387
Glu Asn Met Cys Trp Arg Ile Trp Asn Leu Ala Arg Gln Lys Lys
            80                  85                  90

CAG CTT GAG GGA GAG CAA GCT CAG TGG ATG GCA AAA CGC CGT CAA       432
Gln Leu Glu Gly Glu Gln Ala Gln Trp Met Ala Lys Arg Arg Gln
            95                  100                 105

GAA CGT GAG AGA GGT CGC AGA GAA GCA GTT GCT GAT ATG TCA GAG       477
Glu Arg Glu Arg Gly Arg Arg Glu Ala Val Ala Asp Met Ser Glu
            110                 115                 120

GAT CTA TCT GAG GGA GAG AAA GGA GAT ATA GTC GCT GAC ATG TCA       522
```

-continued

```
Asp Leu Ser Glu Gly Glu Lys Gly Asp Ile Val Ala Asp Met Ser
            125                 130                 135

TCT CAT GGT GAA AGT ACC AGA GGC CGA TTG CCT AGA ATC AGT TCT    567
Ser His Gly Glu Ser Thr Arg Gly Arg Leu Pro Arg Ile Ser Ser
            140                 145                 150

GTT GAG ACA ATG GAA GCA TGG GTC AGT CAG CAG AGA GGA AAG AAG    612
Val Glu Thr Met Glu Ala Trp Val Ser Gln Gln Arg Gly Lys Lys
            155                 160                 165

CTT TAT ATC GTG CTT ATA AGT TTA CAT GGT TTA ATT CGG GGT GAG    657
Leu Tyr Ile Val Leu Ile Ser Leu His Gly Leu Ile Arg Gly Glu
            170                 175                 180

AAT ATG GAG CTT GGA CGG GAT TCT GAT ACT GGT GGT CAG GTG AAG    702
Asn Met Glu Leu Gly Arg Asp Ser Asp Thr Gly Gly Gln Val Lys
            185                 190                 195

TAT GTA GTT GGA GCA ACT GTT GCA CAA GGT CGT TTG TCA AAG GAT    747
Tyr Val Val Gly Ala Thr Val Ala Gln Gly Arg Leu Ser Lys Asp
            200                 205                 210

GAA ATA AAC TCA ACC TAC AAG ATA ATG CGG AGA ATA GAG GCT GAA    792
Glu Ile Asn Ser Thr Tyr Lys Ile Met Arg Arg Ile Glu Ala Glu
            215                 220                 225

GAA TTA ACT CTT GAT GCT TCC GAA ATT GTC ATC ACT AGT ACA AGA    837
Glu Leu Thr Leu Asp Ala Ser Glu Ile Val Ile Thr Ser Thr Arg
            230                 235                 240

CAG GAG ATT GAC GAG CAA TGG CGT TTG TAT GAT GGG TTT GAT CCA    882
Gln Glu Ile Asp Glu Gln Trp Arg Leu Tyr Asp Gly Phe Asp Pro
            245                 250                 255

ATA TTA GAG CGT AAG TTA CGT GCA AGG ATC AAG CGC AAT GTC AGC    927
Ile Leu Glu Arg Lys Leu Arg Ala Arg Ile Lys Arg Asn Val Ser
            260                 265                 270

TGT TAT GGC AGG TTT ATG CCT CGT ATG GCT GTA ATT CCT CCT GGG    972
Cys Tyr Gly Arg Phe Met Pro Arg Met Ala Val Ile Pro Pro Gly
            275                 280                 285

ATG GAG TTC CAC CAT ATT GTG CCA CAT GAA GGT GAC ATG GAT GGT   1017
Met Glu Phe His His Ile Val Pro His Glu Gly Asp Met Asp Gly
            290                 295                 300

GAA ACA GAA GGA AGT GAA GAT GGA AAG ACC CCG GAT CCA CCT ATT   1062
Glu Thr Glu Gly Ser Glu Asp Gly Lys Thr Pro Asp Pro Pro Ile
            305                 310                 315

TGG GCA GAG ATT ATG CGC TTC TTT TCT AAT CCA AGG AAG CCT ATG   1107
Trp Ala Glu Ile Met Arg Phe Phe Ser Asn Pro Arg Lys Pro Met
            320                 330                 335

ATA CTC GCA CTT GCT AGG CCT GAT CCC AAG AAG AAC CTC ACT ACT   1152
Ile Leu Ala Leu Ala Arg Pro Asp Pro Lys Lys Asn Leu Thr Thr
            340                 345                 350

TTA GTG AAA GCA TTT GGT GAA TGT CGT CCA TTG AGA GAC CTT GCT   1197
Leu Val Lys Ala Phe Gly Glu Cys Arg Pro Leu Arg Asp Leu Ala
            355                 360                 365

AAT CTT ACT TTG ATA ATG GGT AAT CGA GAT AAT ATC GAC GAA ATG   1242
Asn Leu Thr Leu Ile Met Gly Asn Arg Asp Asn Ile Asp Glu Met
            370                 375                 380

TCT AGC ACC AAT TCT GCA CTT CTT CTT TCA ATC TTG AAG ATG ATA   1287
Ser Ser Thr Asn Ser Ala Leu Leu Leu Ser Ile Leu Lys Met Ile
            385                 390                 395

GAT AAG TAT GAT CTT TAT GGT CTA GTA GCT TAT CCT AAA CAC CAC   1332
Asp Lys Tyr Asp Leu Tyr Gly Leu Val Ala Tyr Pro Lys His His
            400                 405                 410

AAG CAG TCA GAT GTT CCT GAT ATC TAC CGT CTT GCT GCA AAG ACT   1377
Lys Gln Ser Asp Val Pro Asp Ile Tyr Arg Leu Ala Ala Lys Thr
            415                 420                 425

AAG GGT GTT TTT ATT AAT CCA GCT TTT ATT GAG CCT TTT GGA CTG   1422
```

```
                Lys Gly Val Phe Ile Asn Pro Ala Phe Ile Glu Pro Phe Gly Leu
                                430                 435                 440

ACT TTG ATT GAG GCA GCA GCT TAT GGT CTC CCA ATG GTA GCC ACA              1467
Thr Leu Ile Glu Ala Ala Ala Tyr Gly Leu Pro Met Val Ala Thr
                445                 450                 455

AAA AAT GGA GGA CCT GTT GAT ATA CAT AGG GTT CTT GAC AAT GGT              1512
Lys Asn Gly Gly Pro Val Asp Ile His Arg Val Leu Asp Asn Gly
                460                 465                 470

CTC TTA GTG GAT CCC CAT GAT CAG CAG GCA ATT GCT GAT GCT CTT              1557
Leu Leu Val Asp Pro His Asp Gln Gln Ala Ile Ala Asp Ala Leu
                475                 480                 485

TTG AAG TTG GTT GCT GAT AAG CAA CTG TGG GCT AAA TGC AGG GCA              1602
Leu Lys Leu Val Ala Asp Lys Gln Leu Trp Ala Lys Cys Arg Ala
                490                 495                 500

AAT GGA TTA AAA AAT ATC CAC CTT TTC TCA TGG CCC GAG CAC TGT              1647
Asn Gly Leu Lys Asn Ile His Leu Phe Ser Trp Pro Glu His Cys
                505                 510                 515

AAA ACT TAT CTA TCC CGG ATA GCT AGC TGC AAA CCG AGG CAA CAT              1692
Lys Thr Tyr Leu Ser Arg Ile Ala Ser Cys Lys Pro Arg Gln His
                520                 525                 530

TCC TTG AGA GAT ATT CAT GAT ATA TCT CTG AAT TTG AGA TTT TCA              1737
Ser Leu Arg Asp Ile His Asp Ile Ser Leu Asn Leu Arg Phe Ser
                535                 540                 540

TTA GAT GGG GAA AAG AAT GAC AAT AAA GAA AAT GCT GAT AAT ACA              1782
Leu Asp Gly Glu Lys Asn Asp Asn Lys Glu Asn Ala Asp Asn Thr
                545                 550                 555

TTA GAC CCC GAA GTT CGA AGG AGC AAG TTA GAG AAT GCT GTT TTG              1827
Leu Asp Pro Glu Val Arg Arg Ser Lys Leu Glu Asn Ala Val Leu
                560                 565                 570

TCC TTA TCT AAG GGT GCA CTG AAG AGC ACA TCA AAA TCT TGG TCG              1872
Ser Leu Ser Lys Gly Ala Leu Lys Ser Thr Ser Lys Ser Trp Ser
                575                 580                 585

TCA GAC AAG GCA GAC CAA AAT CCT GGT GCT GGT AAA TTC CCA GCG              1917
Ser Asp Lys Ala Asp Gln Asn Pro Gly Ala Gly Lys Phe Pro Ala
                590                 595                 600

ATT AGG AGG AGG CGA CAT ATT TTT GTT ATT GCA GTG GAT TGT GAT              1962
Ile Arg Arg Arg Arg His Ile Phe Val Ile Ala Val Asp Cys Asp
                605                 610                 615

GCT AGC TCA GGA CTC TCT GGA AGT ATG AAA AAG ATA TTT GAG GCT              2007
Ala Ser Ser Gly Leu Ser Gly Ser Met Lys Lys Ile Phe Glu Ala
                620                 625                 630

GTA GAG AAG GAA AGG GCA GAG GGT TCC ATT GGA TTT ATC CTT GCT              2052
Val Glu Lys Glu Arg Ala Glu Gly Ser Ile Gly Phe Ile Leu Ala
                635                 640                 645

ACA TCT TTC AAT ATA TCA GAA GTA CAG TCT TTC CTG CTT TCA GAG              2097
Thr Ser Phe Asn Ile Ser Glu Val Gln Ser Phe Leu Leu Ser Glu
                650                 655                 660

GGC ATG AAT CCT ACT GAG CAA AAT CCT TTT GTA GTT GAC TTG TAC              2142
Gly Met Asn Pro Thr Glu Gln Asn Pro Phe Val Val Asp Leu Tyr
                665                 670                 675

TAT CAC TCA CAT ATT GAG TAT CGT TGG GGG GGC GAA GGG TTG AGA              2187
Tyr His Ser His Ile Glu Tyr Arg Trp Gly Gly Glu Gly Leu Arg
                680                 685                 690

AAG ACT TTG GTG CGT TGG GCC GCC TCT ATC ATT GAT AAG AAT GGT              2232
Lys Thr Leu Val Arg Trp Ala Ala Ser Ile Ile Asp Lys Asn Gly
                695                 700                 705

GAA AAT GGA GAT CAC ATT GTT GTT GAG GAT GAA GAC AAT TCA GCT              2277
Glu Asn Gly Asp His Ile Val Val Glu Asp Glu Asp Asn Ser Ala
                710                 715                 720

GAC TAC TGC TAT ACA TTC AAA GTT TGC AAG CCT GGG ACG GTT CCT              2322
```

-continued

| | | | | | | | | | | | | |
|---|---|---|---|---|---|---|---|---|---|---|---|---|
|Asp|Tyr|Cys|Tyr|Thr|Phe|Lys|Val|Cys|Lys|Pro|Gly|Thr|Val|Pro|
| | | | |725| | | |730| | | | |735|

```
CCA TCT AAA GAA CTT AGA AAA GTA ATG CGA ATT CAG GCA CTT CGT      2367
Pro Ser Lys Glu Leu Arg Lys Val Met Arg Ile Gln Ala Leu Arg
                740                 745                 750

TGT CAC GCT GTT TAT TGT CAA AAT GGG AGT AGG ATT AAT GTG ATC      2412
Cys His Ala Val Tyr Cys Gln Asn Gly Ser Arg Ile Asn Val Ile
                755                 760                 765

CCT GTA CTG GCA TCT CGG TCC CAA GCA CTC AGG TAC TTA TAT CTG      2457
Pro Val Leu Ala Ser Arg Ser Gln Ala Leu Arg Tyr Leu Tyr Leu
                770                 775                 780

CGA TGG GGA ATG GTC CCT GTA CTG GCA TCT CGG TCC CAA GCA CTC      2502
Arg Trp Gly Met Val Pro Val Leu Ala Ser Arg Ser Gln Ala Leu
                785                 790                 795

AGG TAC TTA TAT CTG CGA TGG GGA ATG GTC CCT GTA CTG GCA TCT      2547
Arg Tyr Leu Tyr Leu Arg Trp Gly Met Val Pro Val Leu Ala Ser
                800                 805                 810

CGG TCC CAA GCA CTC AGG TAC TTA TAT CTG CGA TGG GGA ATG GAC      2592
Arg Ser Gln Ala Leu Arg Tyr Leu Tyr Leu Arg Trp Gly Met Asp
                815                 820                 825

TTG TCG AAG TTG GTG GTT TTC GTC GGA GAA AGT GGT GAT ACC GAT      2637
Leu Ser Lys Leu Val Val Phe Val Gly Glu Ser Gly Asp Thr Asp
                830                 835                 840

TAT GAA GGA TTG ATC GGT GGT CTA CGC AAG GCT GTC ATA ATG AAA      2682
Tyr Glu Gly Leu Ile Gly Gly Leu Arg Lys Ala Val Ile Met Lys
                845                 850                 855

GGA CTC TGC ACT AAT GCA AGC AGC TTA ATT CAC GGT AAT AGG AAT      2727
Gly Leu Cys Thr Asn Ala Ser Ser Leu Ile His Gly Asn Arg Asn
                860                 865                 870

TAC CCG CTA TCT GAT GTT TTA CCA TTC GAG AGC CCT AAT GTC ATC      2772
Tyr Pro Leu Ser Asp Val Leu Pro Phe Glu Ser Pro Asn Val Ile
                875                 880                 885

CAA GCG GAT GAG GAA TGT AGC AGC ACC GGA ATC CGT TCC TTA CTG      2817
Gln Ala Asp Glu Glu Cys Ser Ser Thr Gly Ile Arg Ser Leu Leu
                905                 910                 915

GAG AAA CTA GCG GTA CTC AAA GGA TAA TACCCTTCCC CCTTTGATTG        2864
Glu Lys Leu Ala Val Leu Lys Gly End
                920

TCAAAAACCT ATATGAGCTA AGATTATGCC ATGAAAAGAA TGGCCATCCA TTTGGCTTGT 2924

CTTTTG  2930
```

All sequences are cDNA sequences and stem from a cDNA library of leaf tissue. The expression gene is the same in various plant tissues. As a promoter, there can generally be used any promoter which is active in plants. The promoter should ensure that the foreign gene is expressed in the plant. The promoter can be chosen so that the expression occurs only in specified tissues, at a determined time point in the plant's development or at a time point determined by outside influences. The promoter can be homologous or heterologous to the plant. Suitable promoters are e.g. the promoter of the 35S RNA of the cauliflower mosaic virus, the patatin promoter B33 (Rocha-Sosa et al. (1989) EMBO J 8: 23–29) or a promoter that ensures expression only in photosynthetically active tissues. Other promoters can be used which ensure expression only in specified organs, such as the root, tuber, seed, stem or specified cell types such as mesophyllic, epidermal or transport cells. For hindering cold sweetening, suitable promoters are those which ensure an activation of the transcription is stored in harvested parts of the plants. For this, there can be considered cold induced promoters or such promoters that become active during the transition of the tuber from the phase where it stores material to the phase where it gives up material.

DETAILED DESCRIPTION OF THE INVENTION

Figure 1:
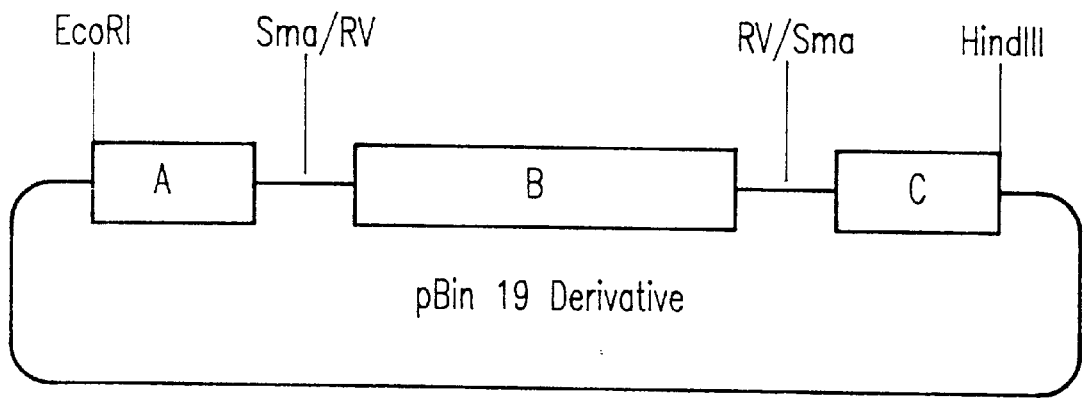
FIG. 1 provides the structure of the 35S-anti-pot-SPS gene.

The coding sequence contains the information for the formation of an mRNA for the sucrose-phosphate-synthase (SPS) or for the formation of an anti-sense RNA for the SPS. Whether the translatable mRNA or an anti-sense RNA is formed depends on the orientation of the coding sequence in relation to the promoter. If the 3' end of the coding sequence is fused to the 3' end of the promoter, an anti-sense RNA results, while the fusion of the 5' end of the coding sequence to the 3' end of the promoter, a translatable RNA results. This latter leads to an increase of the SPS activity in the cell, while the first leads to a reduction of the SPS activity in the cell. Such a reduction of SPS activity is especially significant in view of the undesirable formation of sucrose and/or reducing sugars as a result of cold storage of harvested organs.

The coding sequence for SPS can be one of the three described above or one that is derived by modifications of the sequences described above. A derivation can be carried out, e.g. by current methods of mutagenesis and/or recombination. In particular, changes of SPS sequences are envisaged, that lead to a neutralisation of the plant's own regulation mechanism are contemplated.

The DNA sequences of the invention can also be used for the preparation of derivatives whose gene products are not subjected to the plant's own activity regulation during a phosphorylation reaction.

Further, the sequences can also be used for the preparation of derivatives by targeted and non-targeted mutagenesis.

The invention relates further to derivatives of the DNA sequences of the invention that are obtained by exchange of single bases or by deletion or insertion of base sequences and which code for proteins with a comparable activity to sucrose-phosphate-synthase.

The 5' untranslated area of the sequence, Seq. ID No. 1, is not part of SPS, but is shown as a cloning artefact. The methionine start codon of the coding region lies in a region in which there is no homology of the amino acid sequence to the other SPS sequences. Since this sequence does not also fully coincide in the homologous region with one of the other sequences, it is recognisable that the sequence Seq. ID No 1 is not a derivative of the sequences Sea. ID No. 3 and Seq. ID No 5.

The termination sequence provides the correct finishing of the transcription and the attachment of a polyadenyl group to the RNA. This polyadenyl group has an important function in the stabilisation of RNA molecules in the cells. With suitable plasmids which contain the DNA sequences of the invention, plants can be transformed with the object of raising and/or reducing the SPS activity and/or modifying the sucrose concentration.

Plasmids, that can be used are include p35S-anti-pot-SPS (DSM 7125) and pB33-anti-pot-SPS (DSM 7124). With the gene 35S-anti-pot-SPS, located on the plasmid p35S-anti-pot-SPS, the concentration of the mRNA for the SPS protein and the enzymatic activity, for example, can be reduced. With the gene B33S-anti-pot-SPS, located on the plasmid pB33-anti-pot-SPS, the concentration of the mRNA for the SPS protein and the enzymatic activity, specifically for potato tubers for example, can be reduced. In a similar way to the SPS sequence (Seq. ID No. 1) located on this plasmid, other SPS sequences, e.g. the sequences Seq. ID No. 3 and Seq. ID No. 5 also be cloned in suitable vectors and for the same purpose.

In the plant, the SPS is subjected to an activity control by phosphorylation. This allows the plant to regulate the activity of the enzyme within a fixed frame independent of the amount of the SPS protein. If one of the changes occurring outside the activity of the SPS is to achieved, it is necessary to evade the plant's own regulation mechanism. Therefore changing the phosphorylation possibilities is an important target for influencing the SPS activity and thus the sucrose content of the plant.

It is not known in which position in the SPS protein, target directed changes of the coding regions can be achieved which serve the purpose of introducing in the plant SPS activity which is not subject to any of the plant's own controls.

The DNA sequence described here, which contains the coding region for SPS from *Solanum tuberosum*, allows the identification of the sites of protein phosphorylation of the SPS. By using standard methods (Sambrook, J., Fritsch, E. F., Maniatis, T. (1989) Molecular Cloning: A laboratory Manual, 2nd. Edn., Cold Spring Harbor Laboratory Press, NY, USA), a localisation of the phosphorylation positions of SPS is possible using the DNA sequences of the invention. These being known, by use of the plasmids with the SPS sequence, a target directed mutagenesis (Sambrook et al, 1989) of the coding region of SPS and/or a non-target directed mutagenesis (Sambrook et al, 1989) and subsequent probing of the desired mutations of the coding region of the SPS can be undertaken. Derivatives of the coding region can be prepared with the help of this plasmid, whose derived proteins are not subjected to the plants own regulation mechanisms.

Since the SPS enzyme is regulated by phosphorylation in all tested species, except maize, one can refer to sequence comparisons to identify possible phosphorylation sites. The criterium for this is that a serine residue appears in an acidic medium in the regulated SPS protein, but not however with maize.

There are 12 such serine residues in the sequences, Seq. ID No. 3 and Seq ID No. 5. In the sequence Sea ID No. 1, the first of the 12 serine residues is missing, since the coding region begins just later. The sequence, Seq. ID No. 1 is thus especially suitable for the production of SPS activity in plants that is not liable to endogenous activity regulation.

For the introduction of the SPS sequence in higher plants, a large number of cloning vectors are available which contain a replication signal for *E. coli* and a marker, which allows for the selection of the transformed cells. Examples of vectors are pBR 322, pUC-series, M13 mp-series, pACYC 184; EMBL 3 etc.. According to the introduction method of the desired gene in the plant, other DNA sequences may be suitable. Should the Ti- or Ri-plasmid be used, e.g. for the transformation of the plant cell, then at least the right boundary, often however both the right and left boundary of the Ti- and Ri-Plasmid T-DNA, is attached, as a flanking region, to the gene being introduced. The use of T-DNA for the transformation of plants cells has been intensively researched and is well described in EP 120 516; Hoekama, In: The Binary Plant Vector System, Offset-drukkerij Kanters B.V. Alblasserdam, (1985), Chapter V; Fraley, et al., Crit. Rev. Plant Sci., 4:1–46 and An et al.

(1985) EMBO J. 4: 277–287. Once the introduced DNA is integrated in the genome, it is generally stable there and remains also in the offspring of the original transformed cells. It normally contains a selection marker, which induces resistance in the transformed plant cells against a biocide or antibiotic such as kanamycin, G 418, bleomycin, hygromycin or phosphinotricin etc. The individual marker employed should therefore allow the selection of transformed cells from cells which lack the introduced DNA.

For the introduction of DNA into a plant, besides transformation using Agrobacteria, there are many other techniques available. These techniques include the fusion of protoplasts, microinjection of DNA and electroporation, as well as ballistic methods and virus infection. From the transformed plant material, whole plants can be regenerated in a suitable medium which contains antibiotics or biocides for selection. The resulting plants can then be tested for the presence of introduced DNA. No special demands are placed on the plasmids in injection and electroporation. Simple plasmids, such as e.g. pUC-derivatives can be used. Should however whole plants be regenerated from such transformed cells the presence of a selectable marker gene is necessary. The transformed cells grow within the plants in the usual manner (see also McCormick et al. (1986) Plant Cell Reports 5: 81–84). These plants can be grown normally and crossed with plants, that possess the same transformed genes or different genes. The resulting hybrid individuals have the corresponding phenotypical properties.

Deposits

The following plasmids were deposited at the Deutschen Sammlung von Mikroorganismen (DSM) in Braunschweig, Germany on the Dec. 6, 1992 (deposit number):

Plasmid p35S-anti-pot-SPS (DSM 7125)
Plasmid pB33-anti-pot-SPS (DSM 7124)

DETAILED DESCRIPTION OF THE DRAWINGS

FIG. 1: Structure of the 35S-anti-pot-SPS gene
  A=Fragment A: CaMV 35S promoter, nt 6909–7437 (Franck et al.,1980, Cell 21: 285–294)
  B=Fragment B: sucrose phosphate synthase, EcoRV Fragment (nt 1 bis 2011), ca. 2000 bp, orientation: anti-sense
  C=Fragment C: nt 11748–11939 of the T-DNA of the Ti-plasmid pTiACH5; Gielen et al., 1984, EMBO J 3: 835–846)

Figure 2:
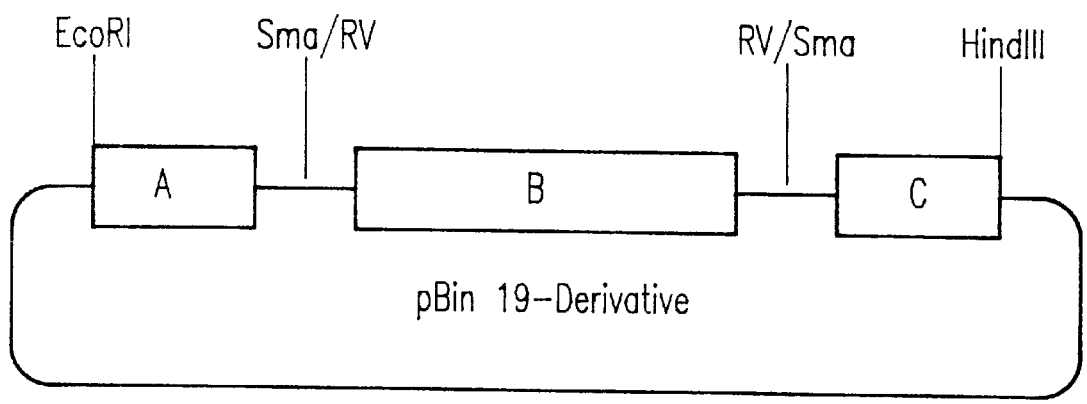
FIG. 2 provides the structure of the B33-anti-pot-SPS gene.

FIG. 2: Structure of the B33-anti-pot-SPS gene
  A=Fragment A: B33 promoter of the patatin gene from S. tuberosum, (Rocha-Sosa et al., 1989, EMBO J 8: 23–29), ca 530 bp
  B=Fragment B: sucrose phosphate synthase (s. FIG. 2), EcoRV fragment (nt 2011 bis 1), ca. 2000 bp, orientation: anti-sense
  C=Fragment C: nt 11748–11939 of T-DNA of the Ti-plasmid pTiACH5 (Gielen et al., 1984, EMBO J 3: 835–846)

Figure 3:
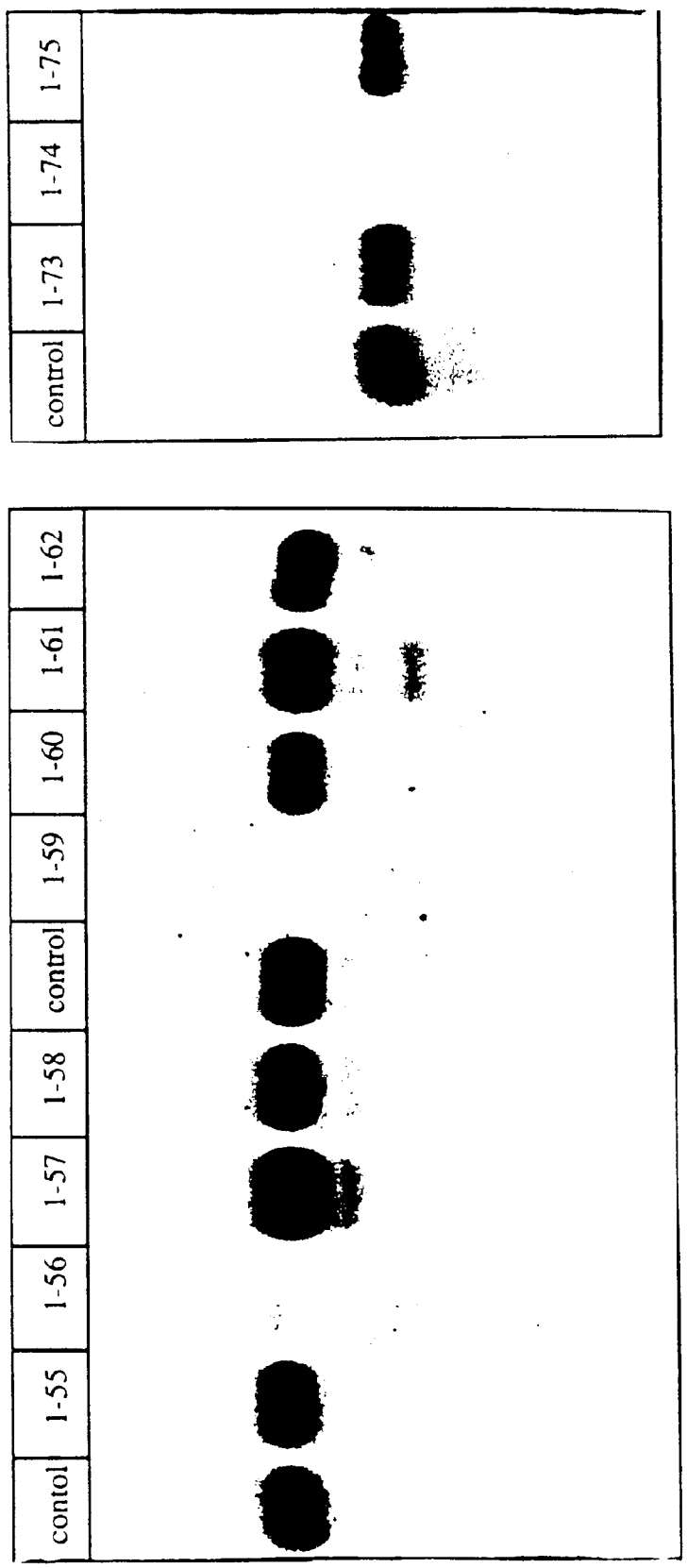
FIG. 3 provides an analysis of plants transformed with a plasmid which included the 35S-anti-pot-SPS gene.
Figure 4:
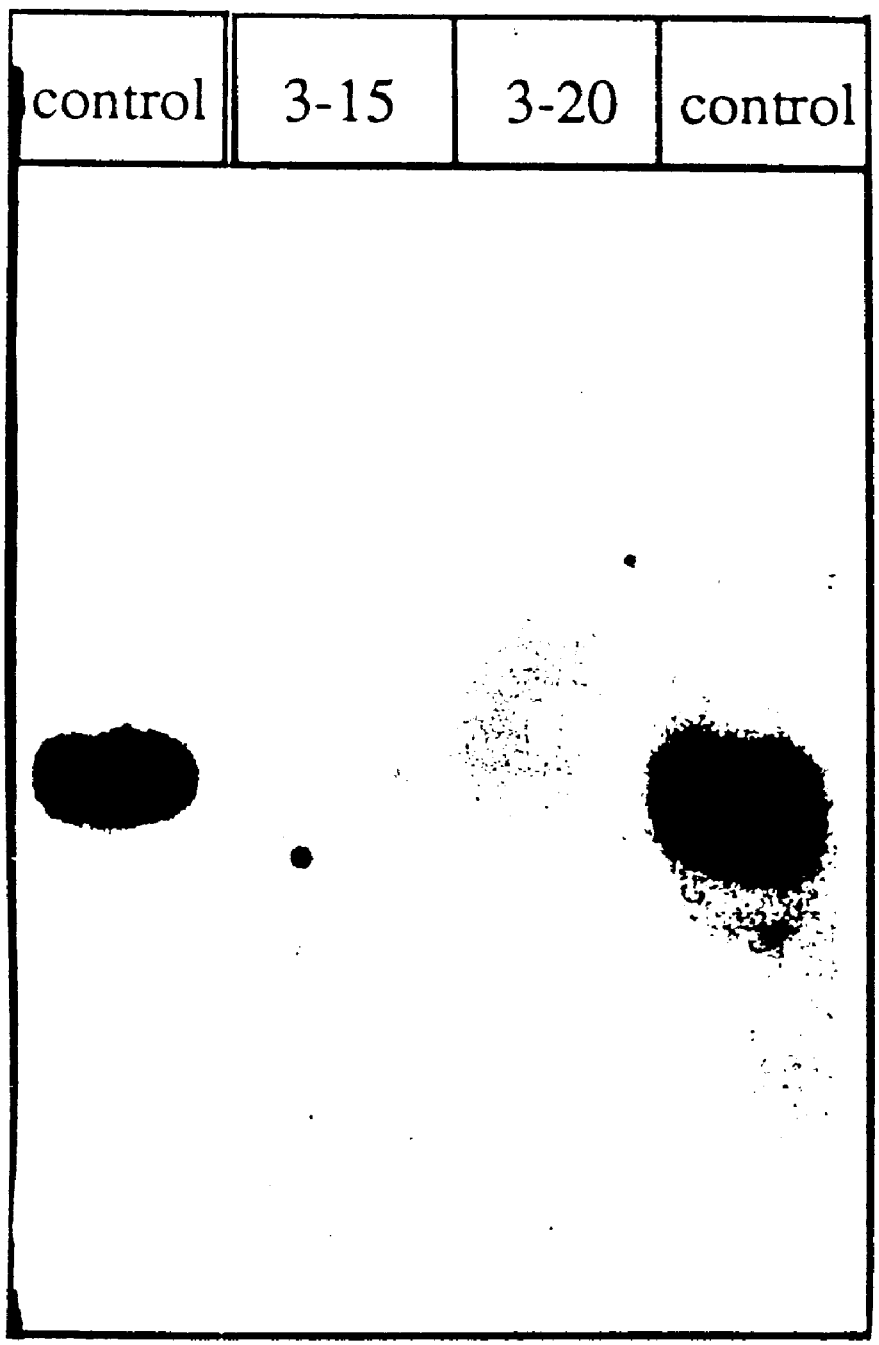
FIG. 4 is an analysis of plants transformed with a plasmid which included the B33-anti-pot-SPS gene.

FIG. 3: shows the results of the transformation of transgenic potato plants.
  Control=wild type plants
  1–75=individual transgenic plants FIG. 4: shows the results of the transformation of potato plants Control=wild type plants
  3–20=individual transgenic plants In order to understand the examples forming the basis of this invention all the processes necessary for these tests and which are known per se will first of all be listed:

1. Cloning Process

The vectors pUC 18/19 and M13mp10 series (Yanisch-Perron et al. (1985) Gene 33: 103–119), as well as the vector EMBL 3 (Frischauf et al. (1983) J Mol Biol 170: 827–842) were used for cloning.

For the plant transformations, the gene constructs were cloned in the binary vector BIN 19 (Bevan (1984) Nucl. Acids Res 12: 8711–8720)

2. Bacterial Strains

The E. coli strain BMH71-18 (Messing et al., Proc. Natl. Acad. Sci. USA (1977), 24, 6342–6346) or TB1 was used for the pUC and M13 mP vectors.

For the vector BIN19, only the E. coli strain TB1 was used. TB1 is a recombinant-negative, tetracycline-resistant derivative of strain JM101 (Yanisch-Perron et al., Gene (1985), 33, 103–119). The genotype of the TB1 strain is (Bart Barrel, personal communication): F'(traD36, proAB, laci, lacZΔM15), Δ(lac, pro), SupE, this, recA, Sr1::Tn10 (TcR).

The transformation of the plasmids into the potato plants was carried out using Agrobacterium tumefaciens strain LBA4404 (Bevan, (1984), Nucl. Acids Res. 12, 8711–8720).

3. Transformation of Agrobacterium tumefaciens

In the case of BIN19 derivatives, the insertion of the DNA into the Agrobacterium was effected by direct transformation in accordance with the method of Holsters et al., (1978) (Mol Gene Genet 163: 181–187). The plasmid DNA of the transformed Agrobacterium was isolated in accordance with the method of Birnboim and Doly (1979) (Nucl Acids Res 7: 1513–1523) and was analysed by gel electrophoresis after suitable restriction cleavage.

4. Plant Transformation

Ten small leaves, wounded with a scalpel, of a sterile potato culture were placed in 10 ml of MS medium with 2% sucrose containing 30–50 μl of an Agrobacterium tumefaciens overnight culture grown under selection. After 3–5 minutes gentle shaking, the leaves were laid out on MS medium of 1.6% glucose, 2 mg/l of zeatin ribose, 0.02 mg/l of naphthylacetic acid, 0.02 mg/l of gibberellic acid, 500 mg/l of claforan, 50 mg/l of kanamycin and 0.8% bacto agar. After incubation for one week at 25° C. and 3000 lux, the claforan concentration in the medium was reduced by half.

5. SPS Activity Test

The SPS activity was determined according to the method of Siegel and Stitt (1990, Plant Science 66: 205–210) in a two stage analysis. To 180 μl of a solution of 50 mM HEPES/KOH (pH 7.4), 5 mM magnesium chloride, 5 mM fructose-6-phosphate, 25 mM glucose-6-phosphate and 6 mM uridine-5'-diphosphoglucose 20 μl of probe was added and incubated for 10 minutes at 25° C. It was heated for 3 minutes at 95° C., to complete the reaction. After centrifuging, the supernatant was spectroscopically analysed for the liberation of uridine-5'-diphosphate, whereby a pyruvate-kinase coupling enzyme reaction was used. Preparations without hexose phosphate, as well as the measurement of the recovery of added uridine-5'-diphosphate act as controls.

EXAMPLES

Example 1

Cloning of Genes of the Sucrose-phosphate-synthase from Potato

Poly-A+ RNA was isolated from large leaves of spinach plants as well as potato plants grown in the greenhouse. Resulting from the poly-A+ RNA, a cDNA library in the expression vector Lambda Zap II was laid out. 100,000 plaques of both libraries were separated from spinach using a rabbit antiserum directed against pure SPS protein in relation to immunologically cross reacting protein. (Sonnewald et al., 1992, in press). From the potato library, positively reacting clones were obtained. These clones were further purified by standard methods and, by in vivo excision, plasmids were obtained which carried a double stranded cDNA as an insertion. After testing the size of the insertions, individual clones were analysed by determining the primary sequence.

Example 2

Determination of the Nucleotide Sequence of the SPS from Potato Coding cDNA Molecules and Derivation of the Corresponding Amino Acid Sequences The nucleotide sequences of the insertions obtained from Example 1 were determined by standard methods by means of the dideoxy method (Sanger et al. (1977) Proc. Natl. Acad. Sci. USA, 74, 5463–5467). The nucleotide sequences (Seq. ID No. 1 to Seq. ID No. 3) are described above. The amino acid sequences derived therefrom are also given.

Example 3

Construct of the Plasmid p35s-anti-pot-SPS and Insertion of Gene 35s-anti-pot-SPS in the Genome of Potato Plants The gene 35s-anti-pot-SPS consists of the three fragments A, B and C (see FIG. 1).

The plasmid was prepared as follows:

From the pBluescript plasmid with the total insertion, an approximately 2 kb size fragment was prepared by EcoRV cleavage, and this was cloned in the SmaI cleavage site of the vector pBinAR (Höfgen & Willmitzer, 1990, Plant Sci., 66, 221–230). The vector pBinAR is a derivative of the binary vector BIN 19 (Bevan, 1984, Nucl. Acids Res. 12: 8711–8721) and was transferred using an *Agrobacterium tumefaciens* mediated transformation into potato. Intact, fertile plants were regenerated from the transformed cells.

As a result of the transformation, some transgenic potato plants were shown to have a reduced amount of RNA coding for the potato SPS (see FIG. 3). 50 μg total RNA in a Northern blot experiment was hybridised with the probe for SPS from potato.

Further the plants showed a reduction in SPS activity (see Table I).

Thus, by the transfer and expression of the gene 35s-anti-pot-SPS in potato plants, the amount of mRNA for the SPS protein which is formed, as well as the existing enzymatic activity can be significantly reduced.

Example 4

Construct of Plasmid PB33-anti-pot-SPS and Insertion of Gene B33-anti-pot-SPS in the Genome of Potato Plants The gene B33-anti-pot-SPS consists of the three fragments A, B and C (see FIG. 2). The plasmid was prepared in an analogous method to that described in Example 3, except that a pBin 19 derivative was used as starting vector which contains the B33 promoter of the patatin gene from *Solanum tuberosum* (Rocha-Sosa et al., 1989, EMBO J. 8: 23–29) in place of the 35S promoter of pBinAR.

The gene B33-anti-pot-SPS was transferred into potato plants using an *Agrobacterium tumefaciens* mediated transformation. Intact, fertile plants were regenerated from the transformed cells.

As a result of the transformation, some transgenic potato plants were shown with a reduced amount of RNA coding for the potato SPS (see FIG. 4). 50 μg total RNA in a Northern blot experiment was hybridised with the probe for SPS from potato.

Further the plants also showed a reduction of the SPS activity only in the tubers.

Thus, by the transfer and expression of the gene 35s-anti-pot-SPS in potato plants, the amount of mRNA for the SPS protein which is formed, as well as the existing enzymatic activity can be significantly reduced.

TABLE I

| Results of the transformation of potato plants | | | | |
|---|---|---|---|---|
| 1 | 2 | 3 | 4 | 5 |
| Control | 26.1 | 3.6 | 13.8 | 100 |
| 1-55 | 11.8 | 2.7 | 22.9 | 45 |
| 1-57 | 20.4 | 5.9 | 28.9 | 78 |
| 1-59 | 3.8 | 1.4 | 36.8 | 14.6 |
| 1-67 | 3.8 | 1.7 | 44.7 | 14.6 |
| 1-69 | 17.2 | 2.0 | 11.7 | 67 |
| 1-72 | 14.6 | 1.9 | 13.0 | 56 |
| 1-74 | 5.1 | 1.7 | 33.3 | 19.5 |

Column 1: Control = Wild type plants, numbers indicate individual transgenic plants
Column 2: Maximal speed of the enzyme reaction in the SPS activity test in nmol/min/mg.
Column 3: Speed in the SPS activity test in nmol/min/mg.
Column 4: Activity level of the SPS in %.
Column 5: Residual activity of the SPS in %.

I claim:

1. An isolated DNA molecule from *Solanum tuberosum* which encodes sucrose-phosphate-synthase.

2. The isolated DNA molecule as claimed in claim 1 comprising a nucleic acid sequence selected from the group consisting of SEQ ID NO: 1, 3 and 5.

3. The isolated DNA molecule as claimed in claim 1, which encodes a protein having an amino acid sequence selected from the group consisting of SEQ ID NO: 2, 4 and 6.

4. The plasmid p35S-anti-pot-SPS (DSM 7125).

5. The plasmid pB35-anti-pot-SPS (DSM 7124).

6. A method of producing a plant with modified sucrose metabolism relative to a non-transformed plant comprising the steps of transforming a plant cell with the plasmid of claim 4 or claim 5 and regenerating a plant from the transformed plant cell wherein said plant has reduced sucrose-phosphate-synthase activity and modified sucrose metabolism.

7. A method of producing a tuber plant with modified sucrose metabolism relative to a non-transformed tuber plant comprising the steps of transforming a tuber plant cell with the plasmid of claim 4 or claim 5 and regenerating a tuber plant from the transformed plant cell wherein said plant has reduced sucrose-phosphate-synthase activity and modified sucrose metabolism.

* * * * *

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
      (A) LENGTH: 3740 base pairs
      (B) TYPE: nucleic acid
      (C) STRANDEDNESS: single
      (D) TOPOLOGY: linear (ii) MOLECULE TYPE: cDNA (vi) ORIGINAL SOURCE:
      (A) ORGANISM: Solanum tuberosum (ix) FEATURE:
      (A) NAME/KEY: CDS
      (B) LOCATION: 957..3494
      (D) OTHER INFORMATION: /note= "Sucrose-Phosphate-Synthase"

(xi) SEQUENCE DESCRIPTION: SEQ ID NO:1:

```
CTATTCTCTC CCCTCCTTTT TCTCCTCTCT TCAACCCCAA AACTTCCCTT TCAAAGCCTT      60

TGCTTTCCCT TTCTCACTTA CCCAGATCAA CTAAGCCAAT TTGCTGTAGC CTCAGAAAAC     120

AGCATTCCCA GATTGAAAAA GAATCTTTTT CAGTACCCAA AAGTTGGGTT TCTCATGTCC     180

AGCAAGGATT AGCTGCTCTA GCTATTTCTT TAGCCCTTAA TTTTTGTCCA GTTGTGTCTT     240

CTGATTCTGC ATTGGCATCT GAATTTGATG TGTTAAATGA AGGGCCACCA AAGGACTCAT     300

ATGTAGTTGA TGATGCTGGT GTGCTTAGCA GGGTGACAAA GTCTGATTTG AAGGCATTGT     360

TGTCTGATGT GGAGAAGAGA AAAGGCTTCC ACATTAATTT CATCACTGTC CGCAAGCTCA     420

CTAGCAAAGC TGATGCTTTT GAGTATGCTG ACCAAGTTTT GGAGAAGTGG TACCCTAGTG     480

TTGAACAAGG AAATGATAAG GGTATAGTTG TGCTTGTTAC AAGTCAAAAG GAAGGCGCAA     540

TAACCGGTGG CCCTGATTTT GTAAAGGCCG TTGGAGATAC TGTTCTTGAT GCTACCGTCT     600

CAGAGAACCT TCCAGTGTTG GCTACTGAAG AGAAGTACAA TGAAGCAGTT TTCAGCACTG     660

CCACACGTCT TGTTGCAGCC ATTGATGGCC TTCCTGATCC TGGTGGACCC CAACTCAAGG     720

ATAACAAAAG AGAGTCCAAC TTCAAATCCA GAGAGGAAAC TGATGAGAAA AGAGGACAAT     780

TCACACTTGT GGTTGGTGGG CTGTTAGTGA TTGCTTTTGT TGTTCCTATG GCTCAATACT     840

ATGCATATGT TTCAAAGAAG TGAACTGTCT GATTCTGGAA AGTTACATTT TCGTGAGATT     900

TGAGTAAGCA TGTATATTAT CGTGTACAAA ATGGTCCATT CGGAAATGAC TGATTC       956

ATG AGA TAT TTA AAA AGG ATA AAT ATG AAG ATT TGG ACC TCC CCT AAC     1004
Met Arg Tyr Leu Lys Arg Ile Asn Met Lys Ile Trp Thr Ser Pro Asn
 1               5                  10                  15

ATA ACG GAT ACT GCC ATT TCT TTT TCA GAG ATG CTG ACG CCA ATA AGT     1052
Ile Thr Asp Thr Ala Ile Ser Phe Ser Glu Met Leu Thr Pro Ile Ser
             20                  25                  30

ACA GAC GGC TTG ATG ACT GAG ATG GGG GAG AGT AGT GGT GCT TAT ATT     1100
Thr Asp Gly Leu Met Thr Glu Met Gly Glu Ser Ser Gly Ala Tyr Ile
         35                  40                  45

ATT CGC ATT CCT TTT GGA CCA AGA GAG AAA TAT ATT CCA AAA GAA CAG     1148
Ile Arg Ile Pro Phe Gly Pro Arg Glu Lys Tyr Ile Pro Lys Glu Gln
     50                  55                  60

CTA TGG CCC TAT ATT CCC GAA TTT GTT GAT GGT GCA CTT AAC CAT ATT     1196
Leu Trp Pro Tyr Ile Pro Glu Phe Val Asp Gly Ala Leu Asn His Ile
 65                  70                  75                  80
```

| | | | | | | | | | | | | | | | |
|---|---|---|---|---|---|---|---|---|---|---|---|---|---|---|---|
| ATT | CAA | ATG | TCC | AAA | GTT | CTT | GGG | GAG | CAA | ATT | GGT | AGT | GGC | TAT | CCT | 1244 |
| Ile | Gln | Met | Ser | Lys | Val | Leu | Gly | Glu | Gln | Ile | Gly | Ser | Gly | Tyr | Pro |
| | | | 85 | | | | | 90 | | | | | 95 | | |

| GTG | TGG | CCT | GTT | GCC | ATA | CAC | GGA | CAT | TAT | GCT | GAT | GCT | GGC | GAC | TCA | 1292 |
| Val | Trp | Pro | Val | Ala | Ile | His | Gly | His | Tyr | Ala | Asp | Ala | Gly | Asp | Ser |
| | | 100 | | | | | 105 | | | | | 110 | | | |

| GCT | GCT | CTC | CTG | TCA | GGT | GCT | TTA | AAT | GTA | CCA | ATG | CTT | TTC | ACT | GGT | 1340 |
| Ala | Ala | Leu | Leu | Ser | Gly | Ala | Leu | Asn | Val | Pro | Met | Leu | Phe | Thr | Gly |
| | | 115 | | | | | 120 | | | | | 125 | | | |

| CAC | TCA | CTT | GGT | AGA | GAT | AAG | TTG | GAG | CAA | CTG | TTG | CGA | CAA | GGT | CGT | 1388 |
| His | Ser | Leu | Gly | Arg | Asp | Lys | Leu | Glu | Gln | Leu | Leu | Arg | Gln | Gly | Arg |
| | 130 | | | | | 135 | | | | | 140 | | | | |

| TTG | TCA | AAG | GAT | GAA | ATA | AAC | TCA | ACC | TAC | AAG | ATA | ATG | CGG | AGA | ATA | 1436 |
| Leu | Ser | Lys | Asp | Glu | Ile | Asn | Ser | Thr | Tyr | Lys | Ile | Met | Arg | Arg | Ile |
| 145 | | | | | 150 | | | | | 155 | | | | | 160 |

| GAG | GCT | GAA | GAA | TTA | ACT | CTT | GAT | GCT | TCC | GAA | ATT | GTC | ATC | ACT | AGT | 1484 |
| Glu | Ala | Glu | Glu | Leu | Thr | Leu | Asp | Ala | Ser | Glu | Ile | Val | Ile | Thr | Ser |
| | | | | 165 | | | | | 170 | | | | | 175 | |

| ACA | AGA | CAG | GAG | ATT | GAC | GAG | CAA | TGG | CGT | TTG | TAT | GAT | GGG | TTT | GAT | 1532 |
| Thr | Arg | Gln | Glu | Ile | Asp | Glu | Gln | Trp | Arg | Leu | Tyr | Asp | Gly | Phe | Asp |
| | | | 180 | | | | | 185 | | | | | 190 | | |

| CCA | ATA | TTA | GAG | CGT | AAG | TTA | CGT | GCA | AGG | ATC | AAG | CGC | AAT | GTC | AGC | 1580 |
| Pro | Ile | Leu | Glu | Arg | Lys | Leu | Arg | Ala | Arg | Ile | Lys | Arg | Asn | Val | Ser |
| | | 195 | | | | | 200 | | | | | 205 | | | |

| TGT | TAT | GGC | AGG | TTT | ATG | CCT | CGT | ATG | GCT | GTA | ATT | CCT | CCT | GGG | ATG | 1628 |
| Cys | Tyr | Gly | Arg | Phe | Met | Pro | Arg | Met | Ala | Val | Ile | Pro | Pro | Gly | Met |
| | 210 | | | | | 215 | | | | | 220 | | | | |

| GAG | TTC | CAC | CAT | ATT | GTG | CCA | CAT | GAA | GGT | GAC | ATG | GAT | GGA | GAA | ACA | 1676 |
| Glu | Phe | His | His | Ile | Val | Pro | His | Glu | Gly | Asp | Met | Asp | Gly | Glu | Thr |
| 225 | | | | | 230 | | | | | 235 | | | | | 240 |

| GAA | GGA | AGT | GAA | GAT | GGG | AAG | ACC | CCG | GAT | CCA | CCT | ATT | TGG | GCA | GAG | 1724 |
| Glu | Gly | Ser | Glu | Asp | Gly | Lys | Thr | Pro | Asp | Pro | Pro | Ile | Trp | Ala | Glu |
| | | | | 245 | | | | | 250 | | | | | 255 | |

| ATT | ATG | CGC | TTC | TTT | TCT | AAT | CCA | AGG | AAG | CCT | ATG | ATA | CTC | GCA | CTT | 1772 |
| Ile | Met | Arg | Phe | Phe | Ser | Asn | Pro | Arg | Lys | Pro | Met | Ile | Leu | Ala | Leu |
| | | | 260 | | | | | 265 | | | | | 270 | | |

| GCT | AGG | CCT | GAT | CCC | AAG | AAG | AAC | CTC | ACT | ACT | TTA | GTG | AAA | GCA | TTT | 1820 |
| Ala | Arg | Pro | Asp | Pro | Lys | Lys | Asn | Leu | Thr | Thr | Leu | Val | Lys | Ala | Phe |
| | | 275 | | | | | 280 | | | | | 285 | | | |

| GGT | GAA | TGT | CGT | CCA | TTG | AGA | GAG | CTT | GCT | AAT | CTT | ACT | TTG | ATA | ATG | 1868 |
| Gly | Glu | Cys | Arg | Pro | Leu | Arg | Glu | Leu | Ala | Asn | Leu | Thr | Leu | Ile | Met |
| | 290 | | | | | 295 | | | | | 300 | | | | |

| GGT | AAT | CGA | GAT | AAT | ATC | GAC | GAA | ATG | TCT | AGC | ACC | AAT | TCT | GCA | CTT | 1916 |
| Gly | Asn | Arg | Asp | Asn | Ile | Asp | Glu | Met | Ser | Ser | Thr | Asn | Ser | Ala | Leu |
| 305 | | | | | 310 | | | | | 315 | | | | | 320 |

| CTT | CTT | TCA | ATC | TTG | AAA | ATG | ATA | GAT | AAG | TAT | GAT | CTT | TAT | GGT | CAA | 1964 |
| Leu | Leu | Ser | Ile | Leu | Lys | Met | Ile | Asp | Lys | Tyr | Asp | Leu | Tyr | Gly | Gln |
| | | | | 325 | | | | | 330 | | | | | 335 | |

| GTA | GCT | TAT | CCT | AAA | CAC | CAC | AAG | CAG | TCA | GAT | GTT | CCT | GAT | ATC | TAC | 2012 |
| Val | Ala | Tyr | Pro | Lys | His | His | Lys | Gln | Ser | Asp | Val | Pro | Asp | Ile | Tyr |
| | | | 340 | | | | | 345 | | | | | 350 | | |

| CGT | CTT | GCT | GCA | AAG | ACT | AAG | GGT | GTT | TTT | ATT | AAT | CCA | GCT | TTT | ATT | 2060 |
| Arg | Leu | Ala | Ala | Lys | Thr | Lys | Gly | Val | Phe | Ile | Asn | Pro | Ala | Phe | Ile |
| | | 355 | | | | | 360 | | | | | 365 | | | |

| GAG | CCT | TTT | GGA | CTG | ACT | TTG | ATT | GAG | GCA | GCA | GCT | TAT | GGT | CTC | CCA | 2108 |
| Glu | Pro | Phe | Gly | Leu | Thr | Leu | Ile | Glu | Ala | Ala | Ala | Tyr | Gly | Leu | Pro |
| 370 | | | | | 375 | | | | | 380 | | | | | |

| ATG | GTA | GCC | ACA | AAA | AAT | GGA | GGA | CCT | GTT | GAT | ATA | CAT | AGG | GTT | CTT | 2156 |
| Met | Val | Ala | Thr | Lys | Asn | Gly | Gly | Pro | Val | Asp | Ile | His | Arg | Val | Leu |
| 385 | | | | | 390 | | | | | 395 | | | | | 400 |

```
GAC AAT GGT CTC TTA GTG GAT CCC CAT GAT CAG CAG GCA ATT GCT GAT      2204
Asp Asn Gly Leu Leu Val Asp Pro His Asp Gln Gln Ala Ile Ala Asp
            405                 410                 415

GCT CTT TTG AAG TTG GTT GCT GAT AAG CAA CTG TGG GCT AAA TGC AGG      2252
Ala Leu Leu Lys Leu Val Ala Asp Lys Gln Leu Trp Ala Lys Cys Arg
            420                 425                 430

GCA AAT GGA TTA AAA AAT ATC CAC CTT TTC TCA TGG CCC GAG CAC TGT      2300
Ala Asn Gly Leu Lys Asn Ile His Leu Phe Ser Trp Pro Glu His Cys
            435                 440                 445

AAA ACT TAT CTA TCC CGG ATA GCT AGC TGC AAA CCA AGG CAA CCA CGC      2348
Lys Thr Tyr Leu Ser Arg Ile Ala Ser Cys Lys Pro Arg Gln Pro Arg
            450                 455                 460

TGG CTG AGA TCC ATT GAT GAT GAT GAT GAA AAT TCA GAA ACA GAT TCA      2396
Trp Leu Arg Ser Ile Asp Asp Asp Asp Glu Asn Ser Glu Thr Asp Ser
465                 470                 475                 480

CCT AGT GAT TCC TTG AGA GAT ATT CAT GAT ATA TCT CTG AAT TTG AGA      2444
Pro Ser Asp Ser Leu Arg Asp Ile His Asp Ile Ser Leu Asn Leu Arg
            485                 490                 495

TTT TCA TTA GAT GGG GAA AAG AAT GAC AAT AAA GAA AAT GCT GAT AAT      2492
Phe Ser Leu Asp Gly Glu Lys Asn Asp Asn Lys Glu Asn Ala Asp Asn
            500                 505                 510

ACA TTA GAC CCC GAA GTT CGA AGG AGC AAG TTA GAG AAT GCT GTT TTG      2540
Thr Leu Asp Pro Glu Val Arg Arg Ser Lys Leu Glu Asn Ala Val Leu
            515                 520                 525

TCC TTA TCT AAG GGT GCA CTG AAG AGC ACA TCA AAA TCT TGG TCG TCA      2588
Ser Leu Ser Lys Gly Ala Leu Lys Ser Thr Ser Lys Ser Trp Ser Ser
            530                 535                 540

GAC AAG GCA GAC CAA AAC CCT GGT GCT GGT AAA TTC CCA GCG ATT AGG      2636
Asp Lys Ala Asp Gln Asn Pro Gly Ala Gly Lys Phe Pro Ala Ile Arg
545                 550                 555                 560

AGG AGG CGA CAT ATT TTT GTT ATT GCA GTG GAT TGT GAT GCT AGC TCA      2684
Arg Arg Arg His Ile Phe Val Ile Ala Val Asp Cys Asp Ala Ser Ser
            565                 570                 575

GGA CTC TCT GGA AGT GTG AAA AAG ATA TTT GAG GCT GTA GAG AAG GAA      2732
Gly Leu Ser Gly Ser Val Lys Lys Ile Phe Glu Ala Val Glu Lys Glu
            580                 585                 590

AGG GCA GAG GGT TCC ATT GGA TTT ATC CTG GCT ACA TCT TTC AAT ATA      2780
Arg Ala Glu Gly Ser Ile Gly Phe Ile Leu Ala Thr Ser Phe Asn Ile
            595                 600                 605

TCA GAA GTA CAG TCT TTC CTG CTT TCA GAG GGC ATG AAT CCT ACT GAT      2828
Ser Glu Val Gln Ser Phe Leu Leu Ser Glu Gly Met Asn Pro Thr Asp
610                 615                 620

TTT GAT GCT TAC ATA TGC AAT AGT GGT GGT GAT CTT TAT TAT TCG TCC      2876
Phe Asp Ala Tyr Ile Cys Asn Ser Gly Gly Asp Leu Tyr Tyr Ser Ser
625                 630                 635                 640

TTC CAT TCT GAG CAA AAT CCT TTT GTA GTT GAC TTG TAC TAT CAC TCA      2924
Phe His Ser Glu Gln Asn Pro Phe Val Val Asp Leu Tyr Tyr His Ser
            645                 650                 655

CAT ATT GAG TAT CGT TGG GGG GGC GAA GGA TTG AGA AAG ACT TTG GTG      2972
His Ile Glu Tyr Arg Trp Gly Gly Glu Gly Leu Arg Lys Thr Leu Val
            660                 665                 670

CGT TGG GCC GCC TCT ATC ATT GAT AAG AAT GGT GAA AAT GGA GAT CAC      3020
Arg Trp Ala Ala Ser Ile Ile Asp Lys Asn Gly Glu Asn Gly Asp His
            675                 680                 685

ATT GTT GTT GAG GAT GAA GAC AAT TCA GCT GAC TAC TGC TAT ACT TTC      3068
Ile Val Val Glu Asp Glu Asp Asn Ser Ala Asp Tyr Cys Tyr Thr Phe
            690                 695                 700

AAA GTC TGC AAG CCT GGG ACG GTT CCT CCA TCT AAA GAG CTT AGA AAA      3116
Lys Val Cys Lys Pro Gly Thr Val Pro Pro Ser Lys Glu Leu Arg Lys
705                 710                 715                 720
```

-continued

```
GTA ATG CGA ATT CAG GCA CTT CGT TGT CAC GCT GTT TAT TGT CAA AAT      3164
Val Met Arg Ile Gln Ala Leu Arg Cys His Ala Val Tyr Cys Gln Asn
            725                 730                 735

GGG AGT AGG ATT AAT GTG ATC CCT GTA CTG GCA TCT CGG TCC CAA GCA      3212
Gly Ser Arg Ile Asn Val Ile Pro Val Leu Ala Ser Arg Ser Gln Ala
        740                 745                 750

CTC AGG TAC TTA TAT CTG CGA TGG GGA ATG GAC TTG TCG AAG TTG GTG      3260
Leu Arg Tyr Leu Tyr Leu Arg Trp Gly Met Asp Leu Ser Lys Leu Val
    755                 760                 765

GTT TTC GTC GGA GAA AGT GGT GAT ACC GAT TAT GAA GGA TTA ATC GGT      3308
Val Phe Val Gly Glu Ser Gly Asp Thr Asp Tyr Glu Gly Leu Ile Gly
770                 775                 780

GGT CTA CGC AAG GCT GTC ATA ATG AAA GGC CTC TGC ACT AAT GCA AGC      3356
Gly Leu Arg Lys Ala Val Ile Met Lys Gly Leu Cys Thr Asn Ala Ser
785                 790                 795                 800

AGC TTA ATT CAC GGT AAT AGG AAT TAC CCG CTA TCT GAT GTT TTA CCA      3404
Ser Leu Ile His Gly Asn Arg Asn Tyr Pro Leu Ser Asp Val Leu Pro
            805                 810                 815

TTC GAC AGC CCT AAT GTC ATC CAA GCG GAC GAG GAA TGT AGC AGC ACC      3452
Phe Asp Ser Pro Asn Val Ile Gln Ala Asp Glu Glu Cys Ser Ser Thr
        820                 825                 830

GAA ATC CGT TGC TTA CTG GTG AAA CTA GCG GTA CTC AAA GGA              3494
Glu Ile Arg Cys Leu Leu Val Lys Leu Ala Val Leu Lys Gly
    835                 840                 845

TAATACCCTT CCCCCTTTGA TTGTCAAAAA CCTATATGAG CTATAAGACT ATGCCATGAA    3554

AAGAATGGCC ATCCATTTGG CTTGTCTTTT GAAGCTGTTA ATACTTTTCA ACAGACTACA    3614

AAATGAGATG AGTCCTTTGA TCCTCTTTAA AGGACATAAA AGCTTTATGC AAGAACCAGT    3674

GCTGTAAAGT TATAGAATTT CTTTTGCTAT ATATGACATT CGACAGAACC TGTTCCGGTT    3734

CATCGA                                                               3740
```

(2) INFORMATION FOR SEQ ID NO:2:

(i) SEQUENCE CHARACTERISTICS:
        (A) LENGTH: 846 amino acids
        (B) TYPE: amino acid
        (D) TOPOLOGY: linear (ii) MOLECULE TYPE: protein (xi) SEQUENCE DESCRIPTION: SEQ ID NO:2:

```
Met Arg Tyr Leu Lys Arg Ile Asn Met Lys Ile Trp Thr Ser Pro Asn
1               5                   10                  15

Ile Thr Asp Thr Ala Ile Ser Phe Ser Glu Met Leu Thr Pro Ile Ser
            20                  25                  30

Thr Asp Gly Leu Met Thr Glu Met Gly Glu Ser Ser Gly Ala Tyr Ile
        35                  40                  45

Ile Arg Ile Pro Phe Gly Pro Arg Glu Lys Tyr Ile Pro Lys Glu Gln
    50                  55                  60

Leu Trp Pro Tyr Ile Pro Glu Phe Val Asp Gly Ala Leu Asn His Ile
65                  70                  75                  80

Ile Gln Met Ser Lys Val Leu Gly Glu Gln Ile Gly Ser Gly Tyr Pro
            85                  90                  95

Val Trp Pro Val Ala Ile Gly His Tyr Ala Asp Ala Gly Val Asp Ser
            100                 105                 110

Ala Ala Leu Leu Ser Gly Ala Leu Asn Val Pro Met Leu Phe Thr Gly
        115                 120                 125

His Ser Leu Gly Arg Asp Lys Leu Glu Gln Leu Leu Arg Gln Gly Arg
    130                 135                 140
```

```
Leu Ser Lys Asp Glu Ile Asn Ser Thr Tyr Lys Ile Met Arg Arg Ile
145                 150                 155                 160

Glu Ala Glu Glu Leu Thr Leu Asp Ala Ser Glu Ile Val Ile Thr Ser
            165                 170                 175

Thr Arg Gln Glu Ile Asp Glu Gln Trp Arg Leu Tyr Asp Gly Phe Asp
            180                 185                 190

Pro Ile Leu Glu Arg Lys Leu Arg Ala Arg Ile Lys Arg Asn Val Ser
            195                 200                 205

Cys Tyr Gly Arg Phe Met Pro Arg Met Ala Val Ile Pro Pro Gly Met
            210                 215                 220

Glu Phe His His Ile Val Pro His Glu Gly Asp Met Asp Gly Glu Thr
225                 230                 235                 240

Glu Gly Ser Glu Asp Gly Lys Thr Pro Asp Pro Ile Trp Ala Glu
            245                 250                 255

Ile Met Arg Phe Phe Ser Asn Pro Arg Lys Pro Met Ile Leu Ala Leu
            260                 265                 270

Ala Arg Pro Asp Pro Lys Lys Asn Leu Thr Thr Leu Val Lys Ala Phe
            275                 280                 285

Gly Glu Cys Arg Pro Leu Arg Glu Leu Ala Asn Leu Thr Leu Ile Met
            290                 295                 300

Gly Asn Arg Asp Asn Ile Asp Glu Met Ser Ser Thr Asn Ser Ala Leu
305                 310                 315                 320

Leu Leu Ser Ile Leu Lys Met Ile Asp Lys Tyr Asp Leu Tyr Gly Gln
            325                 330                 335

Val Ala Tyr Pro Lys His His Lys Gln Ser Asp Val Pro Asp Ile Tyr
            340                 345                 350

Arg Leu Ala Ala Lys Thr Lys Gly Val Phe Ile Asn Pro Ala Phe Ile
            355                 360                 365

Glu Pro Phe Gly Leu Thr Leu Ile Glu Ala Ala Tyr Gly Leu Pro
            370                 375                 380

Met Val Ala Thr Lys Asn Gly Gly Pro Val Asp Ile His Arg Val Leu
385                 390                 395                 400

Asp Asn Gly Leu Leu Val Asp Pro His Asp Gln Gln Ala Ile Ala Asp
            405                 410                 415

Ala Leu Leu Lys Leu Val Ala Asp Lys Gln Leu Trp Ala Lys Cys Arg
            420                 425                 430

Ala Asn Gly Leu Lys Asn Ile His Leu Phe Ser Trp Pro Glu His Cys
            435                 440                 445

Lys Thr Tyr Leu Ser Arg Ile Ala Ser Cys Lys Pro Arg Gln Pro Arg
450                 455                 460

Trp Leu Arg Ser Ile Asp Asp Asp Glu Asn Ser Glu Thr Asp Ser
465                 470                 475                 480

Pro Ser Asp Ser Leu Arg Asp Ile His Asp Ile Ser Leu Asn Leu Arg
            485                 490                 495

Phe Ser Leu Asp Gly Glu Lys Asn Asp Asn Lys Glu Asn Ala Asp Asn
            500                 505                 510

Thr Leu Asp Pro Glu Val Arg Arg Ser Lys Leu Glu Asn Ala Val Leu
            515                 520                 525

Ser Leu Ser Lys Gly Ala Leu Lys Ser Thr Ser Lys Ser Trp Ser Ser
            530                 535                 540

Asp Lys Ala Asp Gln Asn Pro Gly Ala Gly Lys Phe Pro Ala Ile Arg
545                 550                 555                 560

Arg Arg Arg His Ile Phe Val Ile Ala Val Asp Cys Asp Ala Ser Ser
```

```
                        565                 570                 575
Gly Leu Ser Gly Ser Val Lys Lys Ile Phe Glu Ala Val Glu Lys Glu
                580                 585                 590

Arg Ala Glu Gly Ser Ile Gly Phe Ile Leu Ala Thr Ser Phe Asn Ile
            595                 600                 605

Ser Glu Val Gln Ser Phe Leu Leu Ser Glu Gly Met Asn Pro Thr Asp
610                 615                 620

Phe Asp Ala Tyr Ile Cys Asn Ser Gly Gly Asp Leu Tyr Tyr Ser Ser
625                 630                 635                 640

Phe His Ser Glu Gln Asn Pro Phe Val Val Asp Leu Tyr Tyr His Ser
                645                 650                 655

His Ile Glu Tyr Arg Trp Gly Gly Gly Leu Arg Lys Thr Leu Val
            660                 665                 670

Arg Trp Ala Ala Ser Ile Ile Asp Lys Asn Gly Glu Asn Gly Asp His
            675                 680                 685

Ile Val Val Glu Asp Glu Asp Asn Ser Ala Asp Tyr Cys Tyr Thr Phe
690                 695                 700

Lys Val Cys Lys Pro Gly Thr Val Pro Pro Ser Lys Glu Leu Arg Lys
705                 710                 715                 720

Val Met Arg Ile Gln Ala Leu Arg Cys His Ala Val Tyr Cys Gln Asn
                725                 730                 735

Gly Ser Arg Ile Asn Val Ile Pro Val Leu Ala Ser Arg Ser Gln Ala
            740                 745                 750

Leu Arg Tyr Leu Tyr Leu Arg Trp Gly Met Asp Leu Ser Lys Leu Val
            755                 760                 765

Val Phe Val Gly Glu Ser Gly Asp Thr Asp Tyr Glu Gly Leu Ile Gly
770                 775                 780

Gly Leu Arg Lys Ala Val Ile Met Lys Gly Leu Cys Thr Asn Ala Ser
785                 790                 795                 800

Ser Leu Ile His Gly Asn Arg Asn Tyr Pro Leu Ser Asp Val Leu Pro
                805                 810                 815

Phe Asp Ser Pro Asn Val Ile Gln Ala Asp Glu Glu Cys Ser Ser Thr
            820                 825                 830

Glu Ile Arg Cys Leu Leu Val Lys Leu Ala Val Leu Lys Gly
            835                 840                 845

(2) INFORMATION FOR SEQ ID NO:3:

(i) SEQUENCE CHARACTERISTICS:
        (A) LENGTH: 3625 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Solanum tuberosum (ix) FEATURE:
        (A) NAME/KEY: CDS
        (B) LOCATION: 121..3282
        (D) OTHER INFORMATION: /note= "Sucrose-Phosphate-Synthase"

(xi) SEQUENCE DESCRIPTION: SEQ ID NO:3:

ATTTTTTTCT CTAAGTTCTC TCTCGCTGTC CTTATCATTT CACCACCTCC ATAAATCTAG      60

AAACATCTTT TCTACTCCGT TAATCTCTCT AGCACACGGC GGAGGAGTGC GGCGGAGGAG     120

ATG GCG GGA AAC GAT TGG ATT AAC AGT TAC TTA GAG GCG ATA CTG GAT       168
Met Ala Gly Asn Asp Trp Ile Asn Ser Tyr Leu Glu Ala Ile Leu Asp
```

|  |  |  |  |  |  |  |  |  |  |  |  |  |  |  |  |
|---|---|---|---|---|---|---|---|---|---|---|---|---|---|---|---|
| 1 |  |  |  | 5 |  |  |  |  | 10 |  |  |  |  | 15 |  |

```
GTT GGA CCA GGG CTA GAT GAT AAG AAG TCA TCG TTG TTG TTG AGA GAA      216
Val Gly Pro Gly Leu Asp Asp Lys Lys Ser Ser Leu Leu Leu Arg Glu
                 20                  25                  30

AGA GGG AGG TTT AGT CCG ACG AGG TAC TTT GTT GAG GAA GTT ATT ACT      264
Arg Gly Arg Phe Ser Pro Thr Arg Tyr Phe Val Glu Glu Val Ile Thr
             35                  40                  45

GGA TTC GAT GAG ACT GAT TTG CAT CGT TCG TGG ATC CGA GCA CAA GCT      312
Gly Phe Asp Glu Thr Asp Leu His Arg Ser Trp Ile Arg Ala Gln Ala
         50                  55                  60

ACT CGG AGT CCG CAG AGA AGG AAT ACT AGG CTC GAG AAT ATG TGC TGG      360
Thr Arg Ser Pro Gln Arg Arg Asn Thr Arg Leu Glu Asn Met Cys Trp
 65                  70                  75                  80

AGG ATT TGG AAT TTG GCT CGC CAG AAA AAG CAG CTT GAG GGA GAG CAA      408
Arg Ile Trp Asn Leu Ala Arg Gln Lys Lys Gln Leu Glu Gly Glu Gln
                 85                  90                  95

GCT CAG TGG ATG GCA AAA CGC CGT CAA GAA CGT GAA AGA GGT CGC AGA      456
Ala Gln Trp Met Ala Lys Arg Arg Gln Glu Arg Glu Arg Gly Arg Arg
            100                 105                 110

GAA GCA GTT GCT GAT ATG TCA GAG GAT CTA TCT GAG GGA GAG AAA GGA      504
Glu Ala Val Ala Asp Met Ser Glu Asp Leu Ser Glu Gly Glu Lys Gly
        115                 120                 125

GAT ATA GTC GCT GAC ATG TCA TCT CAT GGT GAA AGT ACC AGA GGC CGA      552
Asp Ile Val Ala Asp Met Ser Ser His Gly Glu Ser Thr Arg Gly Arg
    130                 135                 140

TTG CCT AGA ATC AGT TCT GTT GAG ACA ATG GAA GCA TGG GTC AGT CAG      600
Leu Pro Arg Ile Ser Ser Val Glu Thr Met Glu Ala Trp Val Ser Gln
145                 150                 155                 160

CAG AGA GGA AAG AAG CTT TAT ATC GTG CTT ATA AGT TTA CAT GGT TTA      648
Gln Arg Gly Lys Lys Leu Tyr Ile Val Leu Ile Ser Leu His Gly Leu
                165                 170                 175

ATT CGG GGT GAG AAT ATG GAG CTT GGA CGG GAT TCT GAT ACT GGT GGT      696
Ile Arg Gly Glu Asn Met Glu Leu Gly Arg Asp Ser Asp Thr Gly Gly
            180                 185                 190

CAG GTG AAG TAT GTT GTT GAA CTT GCG AGG GCC TTA GGG TCG ATG CCA      744
Gln Val Lys Tyr Val Val Glu Leu Ala Arg Ala Leu Gly Ser Met Pro
        195                 200                 205

GGT GTA TAT CGG GTT GAC TTG CTT ACT AGA CAA GTA TCT TCA CCA GAA      792
Gly Val Tyr Arg Val Asp Leu Leu Thr Arg Gln Val Ser Ser Pro Glu
    210                 215                 220

GTA GAT TGG AGC TAT GGT GAG CCG ACA GAG ATG CTG ACG CCA ATA AGT      840
Val Asp Trp Ser Tyr Gly Glu Pro Thr Glu Met Leu Thr Pro Ile Ser
225                 230                 235                 240

ACA GAC GGC TTG ATG ACT GAG ATG GGG GAG AGT AGT GGT GCT TAT ATT      888
Thr Asp Gly Leu Met Thr Glu Met Gly Glu Ser Ser Gly Ala Tyr Ile
                245                 250                 255

ATT CGC ATT CCT TTT GGA CCA AGA GAG AAA TAT ATT CCA AAA GAA CAG      936
Ile Arg Ile Pro Phe Gly Pro Arg Glu Lys Tyr Ile Pro Lys Glu Gln
            260                 265                 270

CTA TGG CCC TAT ATT CCC GAA TTT GTT GAT GGT GCA CTT AAC CAT ATT      984
Leu Trp Pro Tyr Ile Pro Glu Phe Val Asp Gly Ala Leu Asn His Ile
        275                 280                 285

ATT CAA ATG TCC AAA GTT CTT GGG GAG CAA ATT GGT AGT GGC TAT CCT     1032
Ile Gln Met Ser Lys Val Leu Gly Glu Gln Ile Gly Ser Gly Tyr Pro
    290                 295                 300

GTG TGG CCT GTT GCC ATA CAC GGA CAT TAT GCT GAT GCT GGC GAC TCA     1080
Val Trp Pro Val Ala Ile His Gly His Tyr Ala Asp Ala Gly Asp Ser
305                 310                 315                 320

GCT GCT CTC CTG TCA GGT GCT TTA AAT GTA CCA ATG CTT TTC ACT GGT     1128
Ala Ala Leu Leu Ser Gly Ala Leu Asn Val Pro Met Leu Phe Thr Gly
```

-continued

|  |  |  |  |  |  |  |  |  | 325 |  |  |  |  | 330 |  |  |  |  | 335 |  |  |  |  |  |
|---|---|---|---|---|---|---|---|---|---|---|---|---|---|---|---|---|---|---|---|---|---|---|---|---|---|

```
CAC TCA CTT GGT AGA GAT AAG TTG GAG CAA CTG TTG GCA CAA GGT CGA         1176
His Ser Leu Gly Arg Asp Lys Leu Glu Gln Leu Leu Ala Gln Gly Arg
            340                 345                 350

AAG TCA AAG GAT GAA ATA AAC TCA ACC TAC AAG ATA ATG CGG AGA ATA         1224
Lys Ser Lys Asp Glu Ile Asn Ser Thr Tyr Lys Ile Met Arg Arg Ile
        355                 360                 365

GAG GCT GAA GAA TTA ACT CTT GAT GCT TCC GAA ATT GTC ATC ACT AGT         1272
Glu Ala Glu Glu Leu Thr Leu Asp Ala Ser Glu Ile Val Ile Thr Ser
    370                 375                 380

ACA AGA CAG GAG ATT GAC GAG CAA TGG CGT TTG TAT GAT GGG TTT GAT         1320
Thr Arg Gln Glu Ile Asp Glu Gln Trp Arg Leu Tyr Asp Gly Phe Asp
385                 390                 395                 400

CCA ATA TTA GAG CGT AAG TTA CGT GCA AGG ATC AAG CGC AAT GTC AGC         1368
Pro Ile Leu Glu Arg Lys Leu Arg Ala Arg Ile Lys Arg Asn Val Ser
            405                 410                 415

TGT TAT GGC AGG TTT ATG CCT CGT ATG GCT GTA ATT CCT CCT GGG ATG         1416
Cys Tyr Gly Arg Phe Met Pro Arg Met Ala Val Ile Pro Pro Gly Met
        420                 425                 430

GAG TTC CAC CAT ATT GTG CCA CAT GAA GGT GAC ATG GAT GGT GAA ACA         1464
Glu Phe His His Ile Val Pro His Glu Gly Asp Met Asp Gly Glu Thr
    435                 440                 445

GAA GGA AGT GAA GAT GGG AAG ACC CCG GAT CCA CCT ATT TGG GCA GAG         1512
Glu Gly Ser Glu Asp Gly Lys Thr Pro Asp Pro Pro Ile Trp Ala Glu
450                 455                 460

ATT ATG CGC TTC TTT TCT AAT CCA AGG AAG CCT ATG ATA CTC GCA CTT         1560
Ile Met Arg Phe Phe Ser Asn Pro Arg Lys Pro Met Ile Leu Ala Leu
465                 470                 475                 480

GCT AGG CCT GAT CCC AAG AAG AAC CTC ACT ACT TTA GTG AAA GCA TTT         1608
Ala Arg Pro Asp Pro Lys Lys Asn Leu Thr Thr Leu Val Lys Ala Phe
            485                 490                 495

GGT GAA TGT CGT CCA TTG AGA GAG CTT GCT AAT CTT ACT TTG ATA ATG         1656
Gly Glu Cys Arg Pro Leu Arg Glu Leu Ala Asn Leu Thr Leu Ile Met
        500                 505                 510

GGT AAT CGA GAT AAT ATC GAC GAA ATG TCT AGC ACC AAT TCT GCA CTT         1704
Gly Asn Arg Asp Asn Ile Asp Glu Met Ser Ser Thr Asn Ser Ala Leu
    515                 520                 525

CTT CTT TCA ATC TTG AAA ATG ATA GAT AAG TAT GAT CTT TAT GGT CAA         1752
Leu Leu Ser Ile Leu Lys Met Ile Asp Lys Tyr Asp Leu Tyr Gly Gln
530                 535                 540

GTA GCT TAT CCT AAA CAC CAC AAG CAG TCA GAT GTT CCT GAT ATC TAC         1800
Val Ala Tyr Pro Lys His His Lys Gln Ser Asp Val Pro Asp Ile Tyr
545                 550                 555                 560

CGT CTT GCT GCA AAG ACT AAG GGT GTT TTT ATT AAT CCA GCT TTT ATT         1848
Arg Leu Ala Ala Lys Thr Lys Gly Val Phe Ile Asn Pro Ala Phe Ile
            565                 570                 575

GAG CCT TTT GGA CTG ACT TTG ATT GAG GCA GCA GCT TAT GGT CTC CCA         1896
Glu Pro Phe Gly Leu Thr Leu Ile Glu Ala Ala Ala Tyr Gly Leu Pro
        580                 585                 590

ATG GTA GCC ACA AAA AAT GGA GGA CCT GTT GAT ATA CAT AGG GTT CTT         1944
Met Val Ala Thr Lys Asn Gly Gly Pro Val Asp Ile His Arg Val Leu
    595                 600                 605

GAC AAT GGT CTC TTA GTG GAT CCC CAT GAT CAG CAG GCA ATT GCT GAT         1992
Asp Asn Gly Leu Leu Val Asp Pro His Asp Gln Gln Ala Ile Ala Asp
610                 615                 620

GCT CTT TTG AAG TTG GTT GCT GAT AAG CAA CTG TGG GCT AAA TGC AGG         2040
Ala Leu Leu Lys Leu Val Ala Asp Lys Gln Leu Trp Ala Lys Cys Arg
625                 630                 635                 640

GCA AAT GGA TTA AAA AAT ATC CAC CTT TTC TCA TGG CCC GAG CAC TGT         2088
Ala Asn Gly Leu Lys Asn Ile His Leu Phe Ser Trp Pro Glu His Cys
```

-continued

```
              645                 650                 655
AAA ACT TAT CTA TCC CGG ATA GCT AGC TGC AAA CCA AGG CAA CCA CGC    2136
Lys Thr Tyr Leu Ser Arg Ile Ala Ser Cys Lys Pro Arg Gln Pro Arg
                660                 665                 670

TGG CTG AGA TCC ATT GAT GAT GAT GAT GAA AAT TCA GAA ACA GAT TCA    2184
Trp Leu Arg Ser Ile Asp Asp Asp Asp Glu Asn Ser Glu Thr Asp Ser
            675                 680                 685

CCT AGT GAT TCC TTG AGA GAT ATT CAT GAT ATA TCT CTG AAT TTG AGA    2232
Pro Ser Asp Ser Leu Arg Asp Ile His Asp Ile Ser Leu Asn Leu Arg
        690                 695                 700

TTT TCA TTA GAT GGG GAA AAG AAT GAC AAT AAA GAA AAT GCT GAT AAT    2280
Phe Ser Leu Asp Gly Glu Lys Asn Asp Asn Lys Glu Asn Ala Asp Asn
705                 710                 715                 720

ACA TTA GAC CCC GAA GTT CGA AGG AGC AAG TTA GAG AAT GCT GTT TTG    2328
Thr Leu Asp Pro Glu Val Arg Arg Ser Lys Leu Glu Asn Ala Val Leu
                725                 730                 735

TCC TTA TCT AAG GGT GCA CTG AAG AGC ACA TCA AAA TCT TGG TCG TCA    2376
Ser Leu Ser Lys Gly Ala Leu Lys Ser Thr Ser Lys Ser Trp Ser Ser
            740                 745                 750

GAC AAG GCA GAC CAA AAC CCT GGT GCT GGT AAA TTC CCA GCG ATT AGG    2424
Asp Lys Ala Asp Gln Asn Pro Gly Ala Gly Lys Phe Pro Ala Ile Arg
        755                 760                 765

AGG AGG CGA CAT ATT TTT GTT ATT GCA GTG GAT TGT GAT GCT AGC TCA    2472
Arg Arg Arg His Ile Phe Val Ile Ala Val Asp Cys Asp Ala Ser Ser
770                 775                 780

GGA CTC TCT GGA AGT GTG AAA AAG ATA TTT GAG GCT GTA GAG AAG GAA    2520
Gly Leu Ser Gly Ser Val Lys Lys Ile Phe Glu Ala Val Glu Lys Glu
785                 790                 795                 800

AGG GCA GAG GGT TCC ATT GGA TTT ATC CTG GCT ACA TCT TTC AAT ATA    2568
Arg Ala Glu Gly Ser Ile Gly Phe Ile Leu Ala Thr Ser Phe Asn Ile
                805                 810                 815

TCA GAA GTA CAG TCT TTC CTG CTT TCA GAG GGC ATG AAT CCT ACT GAT    2616
Ser Glu Val Gln Ser Phe Leu Leu Ser Glu Gly Met Asn Pro Thr Asp
            820                 825                 830

TTT GAT GCT TAC ATA TGC AAT AGT GGT GGT GAT CTT TAT TAT TCG TCC    2664
Phe Asp Ala Tyr Ile Cys Asn Ser Gly Gly Asp Leu Tyr Tyr Ser Ser
        835                 840                 845

TTC CAT TCT GAG CAA AAT CCT TTT GTA GTT GAC TTG TAC TAT CAC TCA    2712
Phe His Ser Glu Gln Asn Pro Phe Val Val Asp Leu Tyr Tyr His Ser
850                 855                 860

CAT ATT GAG TAT CGT TGG GGG GGC GAA GGA TTG AGA AAG ACT TTG GTG    2760
His Ile Glu Tyr Arg Trp Gly Gly Glu Gly Leu Arg Lys Thr Leu Val
865                 870                 875                 880

CGT TGG GCC GCC TCT ATC ATT GAT AAG AAT GGT GAA AAT GGA GAT CAC    2808
Arg Trp Ala Ala Ser Ile Ile Asp Lys Asn Gly Glu Asn Gly Asp His
                885                 890                 895

ATT GTT GTT GAG GAT GAA GAC AAT TCA GCT GAC TAC TGC TAT ACT TTC    2856
Ile Val Val Glu Asp Glu Asp Asn Ser Ala Asp Tyr Cys Tyr Thr Phe
            900                 905                 910

AAA GTC TGC AAG CCT GGG ACG GTT CCT CCA TCT AAA GAG CTT AGA AAA    2904
Lys Val Cys Lys Pro Gly Thr Val Pro Pro Ser Lys Glu Leu Arg Lys
        915                 920                 925

GTA ATG CGA ATT CAG GCA CTT CGT TGT CAC GCT GTT TAT TGT CAA AAT    2952
Val Met Arg Ile Gln Ala Leu Arg Cys His Ala Val Tyr Cys Gln Asn
930                 935                 940

GGG AGT AGG ATT AAT GTG ATC CCT GTA CTG GCA TCT CGG TCC CAA GCA    3000
Gly Ser Arg Ile Asn Val Ile Pro Val Leu Ala Ser Arg Ser Gln Ala
945                 950                 955                 960

CTC AGG TAC TTA TAT CTG CGA TGG GGA ATG GAC TTG TCG AAG TTG GTG    3048
Leu Arg Tyr Leu Tyr Leu Arg Trp Gly Met Asp Leu Ser Lys Leu Val
```

```
                    965                970                975
GTT TTC GTC GGA GAA AGT GGT GAT ACC GAT TAT GAA GGA TTA ATC GGT      3096
Val Phe Val Gly Glu Ser Gly Asp Thr Asp Tyr Glu Gly Leu Ile Gly
                    980                985                990

GGT CTA CGC AAG GCT GTC ATA ATG AAA GGC CTC TGC ACT AAT GCA AGC      3144
Gly Leu Arg Lys Ala Val Ile Met Lys Gly Leu Cys Thr Asn Ala Ser
            995                1000                1005

AGC TTA ATT CAC GGT AAT AGG AAT TAC CCG CTA TCT GAT GTT TTA CCA      3192
Ser Leu Ile His Gly Asn Arg Asn Tyr Pro Leu Ser Asp Val Leu Pro
        1010                1015                1020

TTC GAC AGC CCT AAT GTC ATC CAA GCG GAC GAG GAA TGT AGC AGC ACC      3240
Phe Asp Ser Pro Asn Val Ile Gln Ala Asp Glu Glu Cys Ser Ser Thr
1025            1030                1035                1040

GAA ATC CGT TGC TTA CTG GAG AAA CTA GCG GTA CTC AAA GGA              3282
Glu Ile Arg Cys Leu Leu Glu Lys Leu Ala Val Leu Lys Gly
            1045                1050

TAATACCCTT CCCCCTTTGA TTGTCAAAAA CCTATATGAG CTATAAGACT ATGCCATGAA    3342

AAGAATGGCC ATCCATTTGG CTTGTCTTTT GAAGCTGTTA ATACTTTTCA ACAGACTACA    3402

AAATGAGATG AGTCCTTTGA TCCTCTTTAA AGGACATAAA AGCTTTATGC AAGAACCAGT    3462

GCTGTAAAGT TATAGAATTT CTTTTGCTAT ATATGACATT CGACAGAACC AGTTCCGGTT    3522

CATCGAGAAA AAGAAATAAA TTTCAACTTA TAAACATGCC TGATCATGTA AATTATCATA    3582

TACATCCATC GGAAGGCATT ATCGATGGGT TATCAGATTT TTT                      3625

(2) INFORMATION FOR SEQ ID NO:4:

(i) SEQUENCE CHARACTERISTICS:
        (A) LENGTH: 1054 amino acids
        (B) TYPE: amino acid
        (D) TOPOLOGY: linear (ii) MOLECULE TYPE: protein (xi) SEQUENCE DESCRIPTION: SEQ ID NO:4:

Met Ala Gly Asn Asp Trp Ile Asn Ser Tyr Leu Glu Ala Ile Leu Asp
1               5                  10                 15

Val Gly Pro Gly Leu Asp Asp Lys Lys Ser Ser Leu Leu Leu Arg Glu
            20                 25                 30

Arg Gly Arg Phe Ser Pro Thr Arg Tyr Phe Val Glu Val Ile Thr
        35                 40                 45

Gly Phe Asp Glu Thr Asp Leu His Arg Ser Trp Ile Arg Ala Gln Ala
    50                 55                 60

Thr Arg Ser Pro Gln Arg Arg Asn Thr Arg Leu Glu Asn Met Cys Trp
65                 70                 75                 80

Arg Ile Trp Asn Leu Ala Arg Gln Lys Lys Gln Leu Glu Gly Glu Gln
                85                 90                 95

Ala Gln Trp Met Ala Lys Arg Arg Gln Glu Arg Glu Arg Gly Arg Arg
            100                105                110

Glu Ala Val Ala Asp Met Ser Glu Asp Leu Ser Glu Gly Glu Lys Gly
        115                120                125

Asp Ile Val Ala Asp Met Ser Ser His Gly Glu Ser Thr Arg Gly Arg
    130                135                140

Leu Pro Arg Ile Ser Ser Val Glu Thr Met Glu Ala Trp Val Ser Gln
145                150                155                160

Gln Arg Gly Lys Lys Leu Tyr Ile Val Leu Ile Ser Leu His Gly Leu
                165                170                175

Ile Arg Gly Glu Asn Met Glu Leu Gly Arg Asp Ser Asp Thr Gly Gly
```

```
                180              185              190
Gln Val Lys Tyr Val Val Glu Leu Ala Arg Ala Leu Gly Ser Met Pro
            195              200              205
Gly Val Tyr Arg Val Asp Leu Leu Thr Arg Gln Val Ser Ser Pro Glu
210              215              220
Val Asp Trp Ser Tyr Gly Glu Pro Thr Glu Met Leu Thr Pro Ile Ser
225              230              235              240
Thr Asp Gly Leu Met Thr Glu Met Gly Glu Ser Ser Gly Ala Tyr Ile
                245              250              255
Ile Arg Ile Pro Phe Gly Pro Arg Glu Lys Tyr Ile Pro Lys Glu Gln
            260              265              270
Leu Trp Pro Tyr Ile Pro Glu Phe Val Asp Gly Ala Leu Asn His Ile
        275              280              285
Ile Gln Met Ser Lys Val Leu Gly Glu Gln Ile Gly Ser Gly Tyr Pro
    290              295              300
Val Trp Pro Val Ala Ile His Gly His Tyr Ala Asp Ala Gly Asp Ser
305              310              315              320
Ala Ala Leu Leu Ser Gly Ala Leu Asn Val Pro Met Leu Phe Thr Gly
                325              330              335
His Ser Leu Gly Arg Asp Lys Leu Glu Gln Leu Leu Ala Gln Gly Arg
            340              345              350
Lys Ser Lys Asp Glu Ile Asn Ser Thr Tyr Lys Ile Met Arg Arg Ile
        355              360              365
Glu Ala Glu Glu Leu Thr Leu Asp Ala Ser Glu Ile Val Ile Thr Ser
    370              375              380
Thr Arg Gln Glu Ile Asp Glu Gln Trp Arg Leu Tyr Asp Gly Phe Asp
385              390              395              400
Pro Ile Leu Glu Arg Lys Leu Arg Ala Arg Ile Lys Arg Asn Val Ser
                405              410              415
Cys Tyr Gly Arg Phe Met Pro Arg Met Ala Val Ile Pro Pro Gly Met
            420              425              430
Glu Phe His His Ile Val Pro His Glu Gly Asp Met Asp Gly Glu Thr
        435              440              445
Glu Gly Ser Glu Asp Gly Lys Thr Pro Asp Pro Ile Trp Ala Glu
    450              455              460
Ile Met Arg Phe Phe Ser Asn Pro Arg Lys Pro Met Ile Leu Ala Leu
465              470              475              480
Ala Arg Pro Asp Pro Lys Lys Asn Leu Thr Thr Leu Val Lys Ala Phe
                485              490              495
Gly Glu Cys Arg Pro Leu Arg Glu Leu Ala Asn Leu Thr Leu Ile Met
            500              505              510
Gly Asn Arg Asp Asn Ile Asp Glu Met Ser Ser Thr Asn Ser Ala Leu
        515              520              525
Leu Leu Ser Ile Leu Lys Met Ile Asp Lys Tyr Asp Leu Tyr Gly Gln
    530              535              540
Val Ala Tyr Pro Lys His His Lys Gln Ser Asp Val Pro Asp Ile Tyr
545              550              555              560
Arg Leu Ala Ala Lys Thr Lys Gly Val Phe Ile Asn Pro Ala Phe Ile
                565              570              575
Glu Pro Phe Gly Leu Thr Leu Ile Glu Ala Ala Ala Tyr Gly Leu Pro
            580              585              590
Met Val Ala Thr Lys Asn Gly Gly Pro Val Asp Ile His Arg Val Leu
        595              600              605
```

-continued

```
Asp Asn Gly Leu Leu Val Asp Pro His Asp Gln Gln Ala Ile Ala Asp
    610                 615                 620
Ala Leu Leu Lys Leu Val Ala Asp Lys Gln Leu Trp Ala Lys Cys Arg
625                 630                 635                 640
Ala Asn Gly Leu Lys Asn Ile His Leu Phe Ser Trp Pro Glu His Cys
                    645                 650                 655
Lys Thr Tyr Leu Ser Arg Ile Ala Ser Cys Lys Pro Arg Gln Pro Arg
                660                 665                 670
Trp Leu Arg Ser Ile Asp Asp Asp Glu Asn Ser Glu Thr Asp Ser
            675                 680                 685
Pro Ser Asp Ser Leu Arg Asp Ile His Asp Ile Ser Leu Asn Leu Arg
690                 695                 700
Phe Ser Leu Asp Gly Glu Lys Asn Asp Asn Lys Glu Asn Ala Asp Asn
705                 710                 715                 720
Thr Leu Asp Pro Glu Val Arg Arg Ser Lys Leu Glu Asn Ala Val Leu
                725                 730                 735
Ser Leu Ser Lys Gly Ala Leu Lys Ser Thr Ser Lys Ser Trp Ser Ser
            740                 745                 750
Asp Lys Ala Asp Gln Asn Pro Gly Ala Gly Lys Phe Pro Ala Ile Arg
    755                 760                 765
Arg Arg Arg His Ile Phe Val Ile Ala Val Asp Cys Asp Ala Ser Ser
770                 775                 780
Gly Leu Ser Gly Ser Val Lys Lys Ile Phe Glu Ala Val Glu Lys Glu
785                 790                 795                 800
Arg Ala Glu Gly Ser Ile Gly Phe Ile Leu Ala Thr Ser Phe Asn Ile
                805                 810                 815
Ser Glu Val Gln Ser Phe Leu Leu Ser Glu Gly Met Asn Pro Thr Asp
            820                 825                 830
Phe Asp Ala Tyr Ile Cys Asn Ser Gly Gly Asp Leu Tyr Tyr Ser Ser
    835                 840                 845
Phe His Ser Glu Gln Asn Pro Phe Val Val Asp Leu Tyr His Ser
850                 855                 860
His Ile Glu Tyr Arg Trp Gly Gly Glu Gly Leu Arg Lys Thr Leu Val
865                 870                 875                 880
Arg Trp Ala Ala Ser Ile Ile Asp Lys Asn Gly Glu Asn Gly Asp His
                885                 890                 895
Ile Val Val Glu Asp Glu Asp Asn Ser Ala Asp Tyr Cys Tyr Thr Phe
            900                 905                 910
Lys Val Cys Lys Pro Gly Thr Val Pro Pro Ser Lys Glu Leu Arg Lys
    915                 920                 925
Val Met Arg Ile Gln Ala Leu Arg Cys His Ala Val Tyr Cys Gln Asn
930                 935                 940
Gly Ser Arg Ile Asn Val Ile Pro Val Leu Ala Ser Arg Ser Gln Ala
945                 950                 955                 960
Leu Arg Tyr Leu Tyr Leu Arg Trp Gly Met Asp Leu Ser Lys Leu Val
                965                 970                 975
Val Phe Val Gly Glu Ser Gly Asp Thr Asp Tyr Glu Gly Leu Ile Gly
            980                 985                 990
Gly Leu Arg Lys Ala Val Ile Met Lys Gly Leu Cys Thr Asn Ala Ser
    995                 1000                1005
Ser Leu Ile His Gly Asn Arg Asn Tyr Pro Leu Ser Asp Val Leu Pro
    1010                1015                1020
Phe Asp Ser Pro Asn Val Ile Gln Ala Asp Glu Glu Cys Ser Ser Thr
1025                1030                1035                1040
```

```
Glu Ile Arg Cys Leu Leu Glu Lys Leu Ala Val Leu Lys Gly
            1045                1050
```

(2) INFORMATION FOR SEQ ID NO:5:

(i) SEQUENCE CHARACTERISTICS:
        (A) LENGTH: 2930 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Solanum tuberosum (ix) FEATURE:
        (A) NAME/KEY: CDS
        (B) LOCATION: 118..2841
        (D) OTHER INFORMATION: /note= "Sucrose-Phosphate-Synthase"

(xi) SEQUENCE DESCRIPTION: SEQ ID NO:5:

```
ATTTTTTTCT CTAAATTCTC TCTCACTGTC CTTATCATTT CACCACCTCC ATAAATCTAG      60

AAACATCTTT TCTATTCCGT TAATCTCTCT AGCACACGGC GGAGTGCGGC GGAGGAG       117

ATG GCG GGA AAC GAC TGG ATT AAC AGT TAC TTA GAG GCG ATA CTG GAT      165
Met Ala Gly Asn Asp Trp Ile Asn Ser Tyr Leu Glu Ala Ile Leu Asp
  1               5                  10                  15

GTA GGA CCA GGG CTA GAT GAT AAG AAA TCA TCG TTG TTG TTG AGA GAA      213
Val Gly Pro Gly Leu Asp Asp Lys Lys Ser Ser Leu Leu Leu Arg Glu
             20                  25                  30

AGA GGG AGG TTT AGT CCG ACG AGG TAC TTT GTT GAG GAA GTT ATT ACT      261
Arg Gly Arg Phe Ser Pro Thr Arg Tyr Phe Val Glu Glu Val Ile Thr
         35                  40                  45

GGA TTC GAT GAG ACT GAT TTG CAT CGC TCG TGG ATC CGA GCA CAA GCT      309
Gly Phe Asp Glu Thr Asp Leu His Arg Ser Trp Ile Arg Ala Gln Ala
     50                  55                  60

ACT CGG AGT CCG CAG GAG AGG AAT ACT AGG CTC GAG AAT ATG TGC TGG      357
Thr Arg Ser Pro Gln Glu Arg Asn Thr Arg Leu Glu Asn Met Cys Trp
 65                  70                  75                  80

AGG ATT TGG AAT TTG GCT CGC CAG AAA AAG CAG CTT GAG GGA GAG CAA      405
Arg Ile Trp Asn Leu Ala Arg Gln Lys Lys Gln Leu Glu Gly Glu Gln
                 85                  90                  95

GCT CAG TGG ATG GCA AAA CGC CGT CAA GAA CGT GAG AGA GGT CGC AGA      453
Ala Gln Trp Met Ala Lys Arg Arg Gln Glu Arg Glu Arg Gly Arg Arg
            100                 105                 110

GAA GCA GTT GCT GAT ATG TCA GAG GAT CTA TCT GAG GGA GAG AAA GGA      501
Glu Ala Val Ala Asp Met Ser Glu Asp Leu Ser Glu Gly Glu Lys Gly
        115                 120                 125

GAT ATA GTC GCT GAC ATG TCA TCT CAT GGT GAA AGT ACC AGA GGC CGA      549
Asp Ile Val Ala Asp Met Ser Ser His Gly Glu Ser Thr Arg Gly Arg
    130                 135                 140

TTG CCT AGA ATC AGT TCT GTT GAG ACA ATG GAA GCA TGG GTC AGT CAG      597
Leu Pro Arg Ile Ser Ser Val Glu Thr Met Glu Ala Trp Val Ser Gln
145                 150                 155                 160

CAG AGA GGA AAG AAG CTT TAT ATC GTG CTT ATA AGT TTA CAT GGT TTA      645
Gln Arg Gly Lys Lys Leu Tyr Ile Val Leu Ile Ser Leu His Gly Leu
                165                 170                 175

ATT CGG GGT GAG AAT ATG GAG CTT GGA CGG GAT TCT GAT ACT GGT GGT      693
Ile Arg Gly Glu Asn Met Glu Leu Gly Arg Asp Ser Asp Thr Gly Gly
            180                 185                 190

CAG GTG AAG TAT GTA GTT GGA GCA ACT GTT GCA CAA GGT CGT TTG TCA      741
Gln Val Lys Tyr Val Val Gly Ala Thr Val Ala Gln Gly Arg Leu Ser
        195                 200                 205
```

-continued

| | |
|---|---|
| AAG GAT GAA ATA AAC TCA ACC TAC AAG ATA ATG CGG AGA ATA GAG GCT<br>Lys Asp Glu Ile Asn Ser Thr Tyr Lys Ile Met Arg Arg Ile Glu Ala<br>210                        215                    220 | 789 |
| GAA GAA TTA ACT CTT GAT GCT TCC GAA ATT GTC ATC ACT AGT ACA AGA<br>Glu Glu Leu Thr Leu Asp Ala Ser Glu Ile Val Ile Thr Ser Thr Arg<br>225                        230                    235                    240 | 837 |
| CAG GAG ATT GAC GAG CAA TGG CGT TTG TAT GAT GGG TTT GAT CCA ATA<br>Gln Glu Ile Asp Glu Gln Trp Arg Leu Tyr Asp Gly Phe Asp Pro Ile<br>                  245                    250                    255 | 885 |
| TTA GAG CGT AAG TTA CGT GCA AGG ATC AAG CGC AAT GTC AGC TGT TAT<br>Leu Glu Arg Lys Leu Arg Ala Arg Ile Lys Arg Asn Val Ser Cys Tyr<br>          260                    265                    270 | 933 |
| GGC AGG TTT ATG CCT CGT ATG GCT GTA ATT CCT CCT GGG ATG GAG TTC<br>Gly Arg Phe Met Pro Arg Met Ala Val Ile Pro Pro Gly Met Glu Phe<br>          275                    280                    285 | 981 |
| CAC CAT ATT GTG CCA CAT GAA GGT GAC ATG GAT GGT GAA ACA GAA GGA<br>His His Ile Val Pro His Glu Gly Asp Met Asp Gly Glu Thr Glu Gly<br>          290                    295                    300 | 1029 |
| AGT GAA GAT GGA AAG ACC CCG GAT CCA CCT ATT TGG GCA GAG ATT ATG<br>Ser Glu Asp Gly Lys Thr Pro Asp Pro Pro Ile Trp Ala Glu Ile Met<br>305                        310                    315                    320 | 1077 |
| CGC TTC TTT TCT AAT CCA AGG AAG CCT ATG ATA CTC GCA CTT GCT AGG<br>Arg Phe Phe Ser Asn Pro Arg Lys Pro Met Ile Leu Ala Leu Ala Arg<br>                  325                    330                    335 | 1125 |
| CCT GAT CCC AAG AAG AAC CTC ACT ACT TTA GTG AAA GCA TTT GGT GAA<br>Pro Asp Pro Lys Lys Asn Leu Thr Thr Leu Val Lys Ala Phe Gly Glu<br>          340                    345                    350 | 1173 |
| TGT CGT CCA TTG AGA GAC CTT GCT AAT CTT ACT TTG ATA ATG GGT AAT<br>Cys Arg Pro Leu Arg Asp Leu Ala Asn Leu Thr Leu Ile Met Gly Asn<br>          355                    360                    365 | 1221 |
| CGA GAT AAT ATC GAC GAA ATG TCT AGC ACC AAT TCT GCA CTT CTT CTT<br>Arg Asp Asn Ile Asp Glu Met Ser Ser Thr Asn Ser Ala Leu Leu Leu<br>370                        375                    380 | 1269 |
| TCA ATC TTG AAG ATG ATA GAT AAG TAT GAT CTT TAT GGT CTA GTA GCT<br>Ser Ile Leu Lys Met Ile Asp Lys Tyr Asp Leu Tyr Gly Leu Val Ala<br>385                        390                    395                    400 | 1317 |
| TAT CCT AAA CAC CAC AAG CAG TCA GAT GTT CCT GAT ATC TAC CGT CTT<br>Tyr Pro Lys His His Lys Gln Ser Asp Val Pro Asp Ile Tyr Arg Leu<br>                  405                    410                    415 | 1365 |
| GCT GCA AAG ACT AAG GGT GTT TTT ATT AAT CCA GCT TTT ATT GAG CCT<br>Ala Ala Lys Thr Lys Gly Val Phe Ile Asn Pro Ala Phe Ile Glu Pro<br>          420                    425                    430 | 1413 |
| TTT GGA CTG ACT TTG ATT GAG GCA GCA GCT TAT GGT CTC CCA ATG GTA<br>Phe Gly Leu Thr Leu Ile Glu Ala Ala Ala Tyr Gly Leu Pro Met Val<br>          435                    440                    445 | 1461 |
| GCC ACA AAA AAT GGA GGA CCT GTT GAT ATA CAT AGG GTT CTT GAC AAT<br>Ala Thr Lys Asn Gly Gly Pro Val Asp Ile His Arg Val Leu Asp Asn<br>450                        455                    460 | 1509 |
| GGT CTC TTA GTG GAT CCC CAT GAT CAG CAG GCA ATT GCT GAT GCT CTT<br>Gly Leu Leu Val Asp Pro His Asp Gln Gln Ala Ile Ala Asp Ala Leu<br>465                        470                    475                    480 | 1557 |
| TTG AAG TTG GTT GCT GAT AAG CAA CTG TGG GCT AAA TGC AGG GCA AAT<br>Leu Lys Leu Val Ala Asp Lys Gln Leu Trp Ala Lys Cys Arg Ala Asn<br>                  485                    490                    495 | 1605 |
| GGA TTA AAA AAT ATC CAC CTT TTC TCA TGG CCC GAG CAC TGT AAA ACT<br>Gly Leu Lys Asn Ile His Leu Phe Ser Trp Pro Glu His Cys Lys Thr<br>          500                    505                    510 | 1653 |
| TAT CTA TCC CGG ATA GCT AGC TGC AAA CCG AGG CAA CAT TCC TTG AGA<br>Tyr Leu Ser Arg Ile Ala Ser Cys Lys Pro Arg Gln His Ser Leu Arg<br>          515                    520                    525 | 1701 |

```
GAT ATT CAT GAT ATA TCT CTG AAT TTG AGA TTT TCA TTA GAT GGG GAA      1749
Asp Ile His Asp Ile Ser Leu Asn Leu Arg Phe Ser Leu Asp Gly Glu
530                 535                 540

AAG AAT GAC AAT AAA GAA AAT GCT GAT AAT ACA TTA GAC CCC GAA GTT      1797
Lys Asn Asp Asn Lys Glu Asn Ala Asp Asn Thr Leu Asp Pro Glu Val
545                 550                 555                 560

CGA AGG AGC AAG TTA GAG AAT GCT GTT TTG TCC TTA TCT AAG GGT GCA      1845
Arg Arg Ser Lys Leu Glu Asn Ala Val Leu Ser Leu Ser Lys Gly Ala
                565                 570                 575

CTG AAG AGC ACA TCA AAA TCT TGG TCG TCA GAC AAG GCA GAC CAA AAT      1893
Leu Lys Ser Thr Ser Lys Ser Trp Ser Ser Asp Lys Ala Asp Gln Asn
                580                 585                 590

CCT GGT GCT GGT AAA TTC CCA GCG ATT AGG AGG AGG CGA CAT ATT TTT      1941
Pro Gly Ala Gly Lys Phe Pro Ala Ile Arg Arg Arg Arg His Ile Phe
                595                 600                 605

GTT ATT GCA GTG GAT TGT GAT GCT AGC TCA GGA CTC TCT GGA AGT ATG      1989
Val Ile Ala Val Asp Cys Asp Ala Ser Ser Gly Leu Ser Gly Ser Met
610                 615                 620

AAA AAG ATA TTT GAG GCT GTA GAG AAG GAA AGG GCA GAG GGT TCC ATT      2037
Lys Lys Ile Phe Glu Ala Val Glu Lys Glu Arg Ala Glu Gly Ser Ile
625                 630                 635                 640

GGA TTT ATC CTT GCT ACA TCT TTC AAT ATA TCA GAA GTA CAG TCT TTC      2085
Gly Phe Ile Leu Ala Thr Ser Phe Asn Ile Ser Glu Val Gln Ser Phe
                645                 650                 655

CTG CTT TCA GAG GGC ATG AAT CCT ACT GAG CAA AAT CCT TTT GTA GTT      2133
Leu Leu Ser Glu Gly Met Asn Pro Thr Glu Gln Asn Pro Phe Val Val
                660                 665                 670

GAC TTG TAC TAT CAC TCA CAT ATT GAG TAT CGT TGG GGG GGC GAA GGG      2181
Asp Leu Tyr Tyr His Ser His Ile Glu Tyr Arg Trp Gly Gly Glu Gly
                675                 680                 685

TTG AGA AAG ACT TTG GTG CGT TGG GCC GCC TCT ATC ATT GAT AAG AAT      2229
Leu Arg Lys Thr Leu Val Arg Trp Ala Ala Ser Ile Ile Asp Lys Asn
690                 695                 700

GGT GAA AAT GGA GAT CAC ATT GTT GTT GAG GAT GAA GAC AAT TCA GCT      2277
Gly Glu Asn Gly Asp His Ile Val Val Glu Asp Glu Asp Asn Ser Ala
705                 710                 715                 720

GAC TAC TGC TAT ACA TTC AAA GTT TGC AAG CCT GGG ACG GTT CCT CCA      2325
Asp Tyr Cys Tyr Thr Phe Lys Val Cys Lys Pro Gly Thr Val Pro Pro
                725                 730                 735

TCT AAA GAA CTT AGA AAA GTA ATG CGA ATT CAG GCA CTT CGT TGT CAC      2373
Ser Lys Glu Leu Arg Lys Val Met Arg Ile Gln Ala Leu Arg Cys His
                740                 745                 750

GCT GTT TAT TGT CAA AAT GGG AGT AGG ATT AAT GTG ATC CCT GTA CTG      2421
Ala Val Tyr Cys Gln Asn Gly Ser Arg Ile Asn Val Ile Pro Val Leu
                755                 760                 765

GCA TCT CGG TCC CAA GCA CTC AGG TAC TTA TAT CTG CGA TGG GGA ATG      2469
Ala Ser Arg Ser Gln Ala Leu Arg Tyr Leu Tyr Leu Arg Trp Gly Met
770                 775                 780

GTC CCT GTA CTG GCA TCT CGG TCC CAA GCA CTC AGG TAC TTA TAT CTG      2517
Val Pro Val Leu Ala Ser Arg Ser Gln Ala Leu Arg Tyr Leu Tyr Leu
785                 790                 795                 800

CGA TGG GGA ATG GTC CCT GTA CTG GCA TCT CGG TCC CAA GCA CTC AGG      2565
Arg Trp Gly Met Val Pro Val Leu Ala Ser Arg Ser Gln Ala Leu Arg
                805                 810                 815

TAC TTA TAT CTG CGA TGG GGA ATG GAC TTG TCG AAG TTG GTG GTT TTC      2613
Tyr Leu Tyr Leu Arg Trp Gly Met Asp Leu Ser Lys Leu Val Val Phe
                820                 825                 830

GTC GGA GAA AGT GGT GAT ACC GAT TAT GAA GGA TTG ATC GGT GGT CTA      2661
Val Gly Glu Ser Gly Asp Thr Asp Tyr Glu Gly Leu Ile Gly Gly Leu
835                 840                 845
```

```
CGC AAG GCT GTC ATA ATG AAA GGA CTC TGC ACT AAT GCA AGC AGC TTA    2709
Arg Lys Ala Val Ile Met Lys Gly Leu Cys Thr Asn Ala Ser Ser Leu
        850                 855                 860

ATT CAC GGT AAT AGG AAT TAC CCG CTA TCT GAT GTT TTA CCA TTC GAG    2757
Ile His Gly Asn Arg Asn Tyr Pro Leu Ser Asp Val Leu Pro Phe Glu
865                 870                 875                 880

AGC CCT AAT GTC ATC CAA GCG GAT GAG GAA TGT AGC AGC ACC GGA ATC    2805
Ser Pro Asn Val Ile Gln Ala Asp Glu Glu Cys Ser Ser Thr Gly Ile
                885                 890                 895

CGT TCC TTA CTG GAG AAA CTA GCG GTA CTC AAA GGA TAATACCCTT         2851
Arg Ser Leu Leu Glu Lys Leu Ala Val Leu Lys Gly
                900                 905

CCCCCTTTGA TTGTCAAAAA CCTATATGAG CTAAGATTAT GCCATGAAAA GAATGGCCAT  2911

CCATTTGGCT TGTCTTTTG                                               2930
```

(2) INFORMATION FOR SEQ ID NO:6:

(i) SEQUENCE CHARACTERISTICS:
       (A) LENGTH: 908 amino acids
       (B) TYPE: amino acid
       (D) TOPOLOGY: linear (ii) MOLECULE TYPE: protein (xi) SEQUENCE DESCRIPTION: SEQ ID NO:6:

```
Met Ala Gly Asn Asp Trp Ile Asn Ser Tyr Leu Glu Ala Ile Leu Asp
1               5                   10                  15

Val Gly Pro Gly Leu Asp Asp Lys Lys Ser Ser Leu Leu Leu Arg Glu
                20                  25                  30

Arg Gly Arg Phe Ser Pro Thr Arg Tyr Phe Val Glu Glu Val Ile Thr
            35                  40                  45

Gly Phe Asp Glu Thr Asp Leu His Arg Ser Trp Ile Arg Ala Gln Ala
        50                  55                  60

Thr Arg Ser Pro Gln Glu Arg Asn Thr Arg Leu Glu Asn Met Cys Trp
65                  70                  75                  80

Arg Ile Trp Asn Leu Ala Arg Gln Lys Lys Gln Leu Glu Gly Glu Gln
                85                  90                  95

Ala Gln Trp Met Ala Lys Arg Arg Gln Glu Arg Glu Arg Gly Arg Arg
            100                 105                 110

Glu Ala Val Ala Asp Met Ser Glu Asp Leu Ser Glu Gly Glu Lys Gly
        115                 120                 125

Asp Ile Val Ala Asp Met Ser Ser His Gly Glu Ser Thr Arg Gly Arg
130                 135                 140

Leu Pro Arg Ile Ser Ser Val Glu Thr Met Glu Ala Trp Val Ser Gln
145                 150                 155                 160

Gln Arg Gly Lys Lys Leu Tyr Ile Val Leu Ile Ser Leu His Gly Leu
                165                 170                 175

Ile Arg Gly Glu Asn Met Glu Leu Gly Arg Asp Ser Asp Thr Gly Gly
            180                 185                 190

Gln Val Lys Tyr Val Val Gly Ala Thr Val Ala Gln Gly Arg Leu Ser
        195                 200                 205

Lys Asp Glu Ile Asn Ser Thr Tyr Lys Ile Met Arg Arg Ile Glu Ala
210                 215                 220

Glu Glu Leu Thr Leu Asp Ala Ser Glu Ile Val Ile Thr Ser Thr Arg
225                 230                 235                 240

Gln Glu Ile Asp Glu Gln Trp Arg Leu Tyr Asp Gly Phe Asp Pro Ile
                245                 250                 255
```

```
Leu Glu Arg Lys Leu Arg Ala Arg Ile Lys Arg Asn Val Ser Cys Tyr
            260                 265                 270
Gly Arg Phe Met Pro Arg Met Ala Val Ile Pro Pro Gly Met Glu Phe
            275                 280                 285
His His Ile Val Pro His Glu Gly Asp Met Asp Gly Glu Thr Glu Gly
            290                 295                 300
Ser Glu Asp Gly Lys Thr Pro Asp Pro Ile Trp Ala Glu Ile Met
305                 310                 315                 320
Arg Phe Phe Ser Asn Pro Arg Lys Pro Met Ile Leu Ala Leu Ala Arg
                    325                 330                 335
Pro Asp Pro Lys Lys Asn Leu Thr Thr Leu Val Lys Ala Phe Gly Glu
                340                 345                 350
Cys Arg Pro Leu Arg Asp Leu Ala Asn Leu Thr Leu Ile Met Gly Asn
            355                 360                 365
Arg Asp Asn Ile Asp Glu Met Ser Ser Thr Asn Ser Ala Leu Leu Leu
            370                 375                 380
Ser Ile Leu Lys Met Ile Asp Lys Tyr Asp Leu Tyr Gly Leu Val Ala
385                 390                 395                 400
Tyr Pro Lys His His Lys Gln Ser Asp Val Pro Asp Ile Tyr Arg Leu
                    405                 410                 415
Ala Ala Lys Thr Lys Gly Val Phe Ile Asn Pro Ala Phe Ile Glu Pro
                420                 425                 430
Phe Gly Leu Thr Leu Ile Glu Ala Ala Tyr Gly Leu Pro Met Val
            435                 440                 445
Ala Thr Lys Asn Gly Gly Pro Val Asp Ile His Arg Val Leu Asp Asn
            450                 455                 460
Gly Leu Leu Val Asp Pro His Asp Gln Gln Ala Ile Ala Asp Ala Leu
465                 470                 475                 480
Leu Lys Leu Val Ala Asp Lys Gln Leu Trp Ala Lys Cys Arg Ala Asn
                    485                 490                 495
Gly Leu Lys Asn Ile His Leu Phe Ser Trp Pro Glu His Cys Lys Thr
                500                 505                 510
Tyr Leu Ser Arg Ile Ala Ser Cys Lys Pro Arg Gln His Ser Leu Arg
            515                 520                 525
Asp Ile His Asp Ile Ser Leu Asn Leu Arg Phe Ser Leu Asp Gly Glu
            530                 535                 540
Lys Asn Asp Asn Lys Glu Asn Ala Asp Asn Thr Leu Asp Pro Glu Val
545                 550                 555                 560
Arg Arg Ser Lys Leu Glu Asn Ala Val Leu Ser Leu Lys Gly Ala
                    565                 570                 575
Leu Lys Ser Thr Ser Lys Ser Trp Ser Ser Asp Lys Ala Asp Gln Asn
                580                 585                 590
Pro Gly Ala Gly Lys Phe Pro Ala Ile Arg Arg Arg His Ile Phe
            595                 600                 605
Val Ile Ala Val Asp Cys Asp Ala Ser Ser Gly Leu Ser Gly Ser Met
            610                 615                 620
Lys Lys Ile Phe Glu Ala Val Glu Lys Glu Arg Ala Glu Gly Ser Ile
625                 630                 635                 640
Gly Phe Ile Leu Ala Thr Ser Phe Asn Ile Ser Glu Val Gln Ser Phe
                    645                 650                 655
Leu Leu Ser Glu Gly Met Asn Pro Thr Glu Gln Asn Pro Phe Val Val
                660                 665                 670
Asp Leu Tyr Tyr His Ser His Ile Glu Tyr Arg Trp Gly Gly Glu Gly
```

```
                             675                 680                 685
     Leu Arg Lys Thr Leu Val Arg Trp Ala Ala Ser Ile Ile Asp Lys Asn
         690                     695                 700

Gly Glu Asn Gly Asp His Ile Val Val Glu Asp Glu Asp Asn Ser Ala
     705                     710                 715                 720

Asp Tyr Cys Tyr Thr Phe Lys Val Cys Lys Pro Gly Thr Val Pro Pro
                         725                 730                 735

Ser Lys Glu Leu Arg Lys Val Met Arg Ile Gln Ala Leu Arg Cys His
                     740                 745                 750

Ala Val Tyr Cys Gln Asn Gly Ser Arg Ile Asn Val Ile Pro Val Leu
                 755                 760                 765

Ala Ser Arg Ser Gln Ala Leu Arg Tyr Leu Tyr Leu Arg Trp Gly Met
             770                 775                 780

Val Pro Val Leu Ala Ser Arg Ser Gln Ala Leu Arg Tyr Leu Tyr Leu
     785                 790                 795                 800

Arg Trp Gly Met Val Pro Val Leu Ala Ser Arg Ser Gln Ala Leu Arg
                     805                 810                 815

Tyr Leu Tyr Leu Arg Trp Gly Met Asp Leu Ser Lys Leu Val Val Phe
                 820                 825                 830

Val Gly Glu Ser Gly Asp Thr Asp Tyr Glu Gly Leu Ile Gly Gly Leu
                 835                 840                 845

Arg Lys Ala Val Ile Met Lys Gly Leu Cys Thr Asn Ala Ser Ser Leu
         850                 855                 860

Ile His Gly Asn Arg Asn Tyr Pro Leu Ser Asp Val Leu Pro Phe Glu
     865                     870                 875                 880

Ser Pro Asn Val Ile Gln Ala Asp Glu Glu Cys Ser Ser Thr Gly Ile
                     885                 890                 895

Arg Ser Leu Leu Glu Lys Leu Ala Val Leu Lys Gly
                 900                 905
```